(12) United States Patent
Turos et al.

(10) Patent No.: US 8,722,937 B2
(45) Date of Patent: May 13, 2014

(54) ASYMMETRIC DISULFIDES AND ARYL-ALKYL DISULFIDES AS ANTI-BACTERIAL AGENTS

(75) Inventors: Edward Turos, Wesley Chapel, FL (US); Kevin D. Revell, Murray, KY (US)

(73) Assignee: University of South Florida, Tampa, FL (US)

( * ) Notice: Subject to any disclaimer, the term of this patent is extended or adjusted under 35 U.S.C. 154(b) by 843 days.

(21) Appl. No.: 11/712,305

(22) Filed: Feb. 27, 2007

(65) Prior Publication Data

US 2008/0182815 A1 Jul. 31, 2008

Related U.S. Application Data

(60) Provisional application No. 60/777,723, filed on Feb. 27, 2006.

(51) Int. Cl.
| | | |
|---|---|---|
| *C07C 321/28* | (2006.01) | |
| *C07C 323/19* | (2006.01) | |
| *C07C 323/20* | (2006.01) | |
| *C07C 323/41* | (2006.01) | |
| *C07C 323/66* | (2006.01) | |
| *C07D 209/32* | (2006.01) | |

(52) U.S. Cl.
USPC ............... 568/23; 548/492; 560/142; 562/23; 562/41

(58) Field of Classification Search
USPC .......... 548/492; 562/23, 41; 560/142; 568/23
See application file for complete search history.

(56) References Cited

U.S. PATENT DOCUMENTS

| | | | | |
|---|---|---|---|---|
| 2,510,893 | A * | 6/1950 | Morton Kleiman | ........... 546/261 |
| 3,723,513 | A * | 3/1973 | Field et al. | ..................... 562/126 |
| 3,838,114 | A | 9/1974 | Lawrence | |
| 4,883,890 | A * | 11/1989 | Field et al. | ....................... 558/61 |
| 6,375,926 | B1 | 4/2002 | Barnes et al. | |
| 6,476,015 | B1 | 11/2002 | Turos et al. | |
| 6,946,458 | B2 | 9/2005 | Turos | |
| 7,026,472 | B2 | 4/2006 | Dou et al. | |
| 2003/0176512 | A1 * | 9/2003 | Kirkpatrick | ................... 514/707 |
| 2003/0191108 | A1 | 10/2003 | Turos | |
| 2003/0220524 | A1 * | 11/2003 | Langler et al. | .................. 568/23 |
| 2004/0167115 | A1 | 8/2004 | Dou et al. | |
| 2006/0160787 | A1 | 7/2006 | Dou et al. | |
| 2006/0252809 | A1 | 11/2006 | Turos et al. | |
| 2007/0265243 | A1 | 11/2007 | Turos et al. | |

FOREIGN PATENT DOCUMENTS

| | | | | |
|---|---|---|---|---|
| JP | 49041326 | A * | 4/1974 | ............. A01N 41/12 |
| JP | 2004099508 | A * | 4/2004 | ............ C07C 319/14 |

OTHER PUBLICATIONS machine translation of JP 2004099508 A, Japan Patent Office, http://dossier1.ipdl.inpit.go.jp, accessed online on Mar 28, 2012.*
Field et al., J. Med. Chem., 1966, 9(3), p. 397-402.*
Miller et al., Science, 1950, 111, p. 719-720.*
Sepanov et al. (Zhurnal Organicheskoi Khimii, 1977, 13(2), p. 370-374.*
Google machine translation 1 of Sepanov et al., https://translate.google.com/, accessed online on Dec. 17, 2013.*
Google machine translation 2 of Sepanov et al, https://translate.google.com/, accessed online on Dec. 17, 2013.*
Alhamadsheh, M.M. et al. *Chemistry & Biology*, 2007, 14: 513-524.
Campbell, J.W. and Cronan, J.E. *Ann. Rev. Microbiol.*, 2001, 55:305-332.
Choi, K-H. et al. *J. Bacteriology*, 2000, 182(2):365-370.
Clarke, K.M. et al. *J. Am. Chem. Soc.*, 2005, 127:11234-11235.
Coates, C. et al. *Bioorg. Med. Chem.*, 2003, 11:193-196.
Daines, R.A. et al. *J. Med. Chem.*, 2003, 46:5-8.
Davies, C. et al. *Structure*, 2000, 8:185-195.
Delcardayre, S.B. et al. *J. Biol. Chem.*, 1998, 273(10):5744-5751.
He, X. And Reynolds, K.A. *Antimicrob. Agents Chemother.*, 2002, 46(5):1310-1318.
He, X. et at *Antimicro. Agents Chemother.*, 2004, 48:3093-3102.
Heath, R.J. and Rock, C.O. *J. Biol. Chem.*, 1996, 271(18):10996-11000.
Heldreth, B. et al. *Bioorg. and Med. Chem.*, 2006, 14:3775-3784.
Higgins, D.L. et al. *Antimicro. Agents Chemother.*, 2005, 49(3):1127-1134.
Jones, P.B. et al. *J. Med. Chem.*, 2000, 43:3304-3314.
Leonardi, R. et al. *J. Biol. Chem.*, 2005, 280:3314-3322.
Li, Y. et al. *J. Bacterial.*, 2005, 187:3795-3799.
Long, T.E. et al. *Bioorg. Med. Chem.*, 2003, 11:1859-1863.
Lowy, F. *New Eng. J Med.*, 1998, 339:520-532.
Marrakchi, H. et al. *Biochem. Soc. Trans.*, 2002, 30(6):1050-1055.
Mishra, R.K. et al. *Bioorg. Med. Chem. Lett.*, 2006, 16(8):2081-2083.
Mishra, R.K. et al. *Organic Lett.*, 2007, 9(4):575-578.
Newton, G.L. et al. *J. Bacteriology*, 1996, 178(7):1990-1995.
Nie, Z. et al. *J. Med. Chem.*, 2005, 48:1596-1609.
Poole, L.B. et al. *Ann. Rev. Pharmacol. Toxic.*, 2004, 44:325-347.
Qiu, X. et al. *Protein Sci.*, 2005, 14:2087-2094.
Revell, K.D. et al. *Bioorg. and Med. Chem*, 2007, 15(6):2453-2467.
Revell, K.D. et al. "N-alkylthio β-lactams: Novel antibiotics that inhibit fatty acid synthesis in *Staphylococococcus aureus* (MRSA) and *Bacillus anthracis* (anthrax)" poster presented at the 7th Winter Conference on Medicinal and Bioorganic Chemistry, Clearwater, Florida, Feb. 27, 2006.
Rock, C.O. and Cronan, J.E., Jr. *Biochim. Biophys. Acta.*, 1996, 1302:1-16.
Scarsdale, J.N. et al. *J. Biol. Chem.*, 2001, 276(23):20516-20522.
Slater-Radosti, C. et al. *J. Antimicrobial Chemother.*, 2001, 48:1-6.
Turos, E. et al. *Bioorg. Med. Chem. Lett.*, 2002, 12:2229-2231.
Turos, E. et al. *Bioorg. Med. Chem. Lett.*, 2007, 17:53-56.
Turos, E. et al. *Bioorg. Med. Chem.*, 2005, 13:6289-6308.
Turos, E. et al. *Tetrahedron*, 2000, 56:5571-5578.
Cronan, J.E., Jr. and Rock, C.O. *in E. Coli and Salmonella typhimurium: Cellular and Molecular Biology* (Neidhardt, F.C. et al. Eds.).

(Continued)

*Primary Examiner* — Shaojia Anna Jiang
*Assistant Examiner* — Jonathan S Lau
(74) *Attorney, Agent, or Firm* — Saliwanchik, Lloyd & Eisenschenk

(57) ABSTRACT

The present invention provides N-alkylthio β-lactams and disulfide compounds (e.g., alkyl-coenzyme A asymmetric disulfides or aryl-alkyl disulfides), compositions containing such compounds, and method of their use as anti-bacterial agents.

28 Claims, 25 Drawing Sheets

(56) References Cited

OTHER PUBLICATIONS

Long, T. "N-thiolated β-lactams: Chemistry and biology of a novel class of antimicrobial agents for MRSA" University of South Florida Dissertation, 2003.

Burnett, D.A. et al. "β-Lactams from esters and sulfenimines: A new route to monobactams" *J. Org. Chem.*, 1986, 51:1929-1930.

Bligh, E.G. and Dyer, W.J. "A rapid method of total lipid extraction and purification" *Can. J. Biochem. Physiol.*, 1959, 37:911-917.

* cited by examiner

2a

2g

32

FIG. 8A
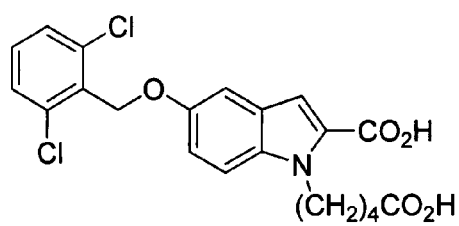
29
FIG. 8B
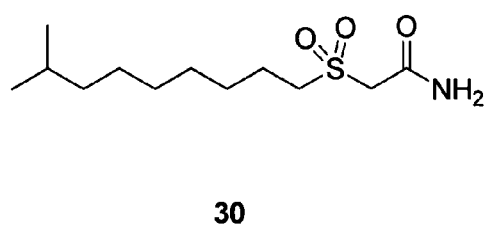
30
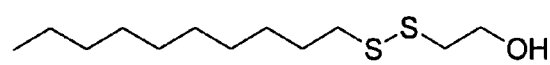
31
FIG. 8C
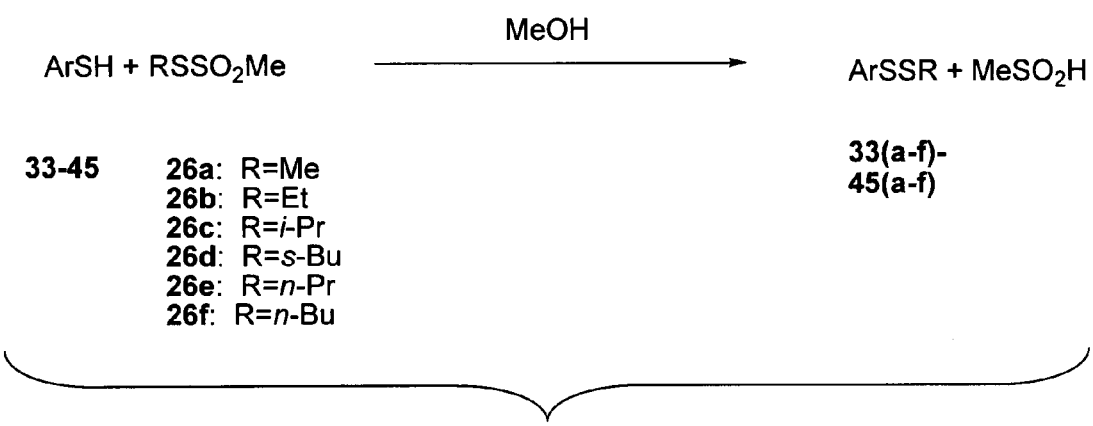
FIG. 10

FIG. 11A  FIG. 11B  FIG. 11C  FIG. 11D  FIG. 11E
 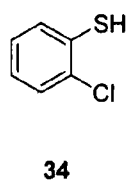 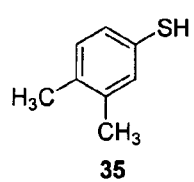 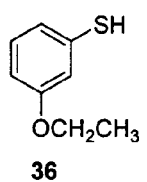 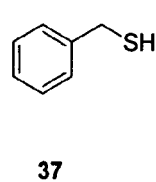
33  34  35  36  37
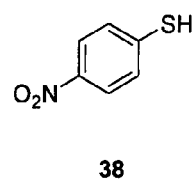 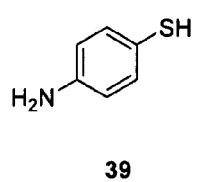 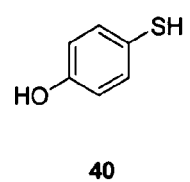 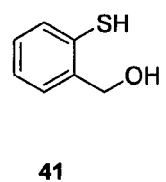 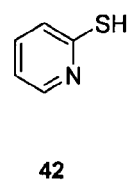
38  39  40  41  42
FIG. 11F  FIG. 11G  FIG. 11H  FIG. 11I  FIG. 11J

25a-f

2a: R = Me
2g: R = s-Bu

FIG. 14A
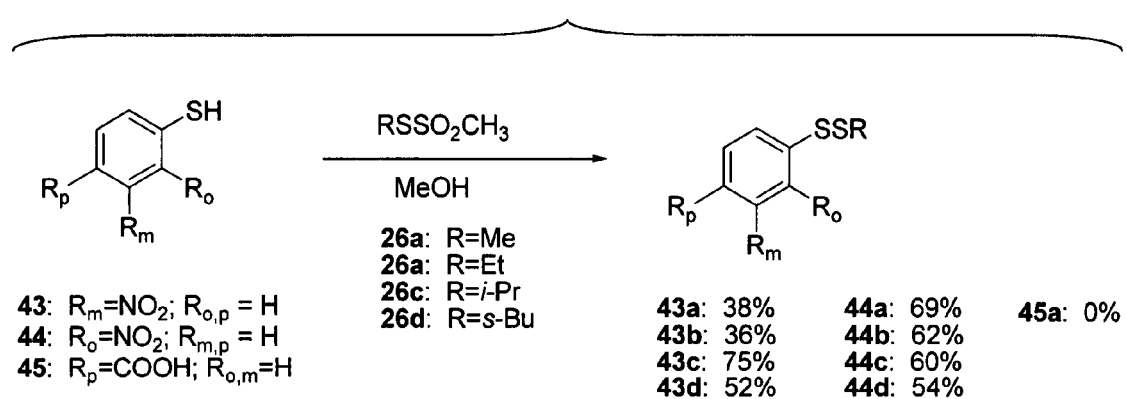
FIG. 14B
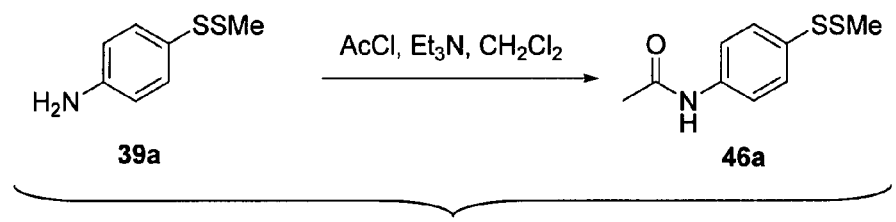
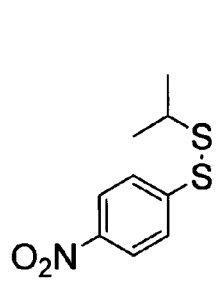    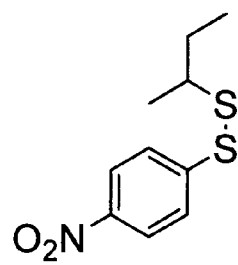
FIG. 15A        FIG. 15B 47: R=SO₃H
48: R=OPO₃H
49: R=OAc
50: R=CO₂Me 51: R=SO₃H
52: R=OPO₃H
53: R=OAc
54: R=CO₂Me

CoA-S-S-R

FIG. 75
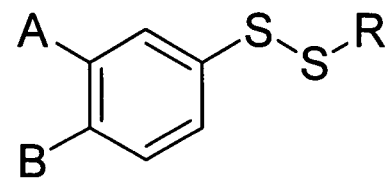
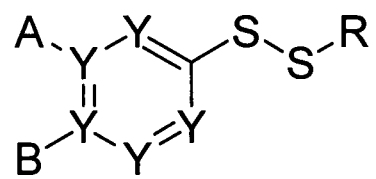
Y = C, N, O
FIG. 76A
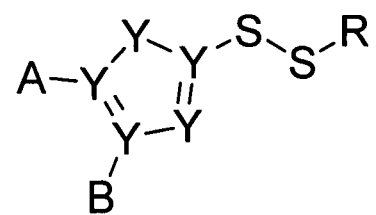
Y = C, N, O, S
FIG. 76B

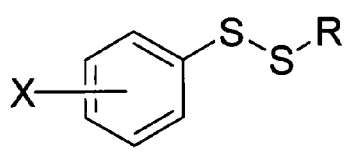
1
FIG. 77
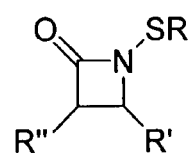
1
FIG. 78A
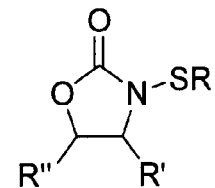
2
FIG. 78B
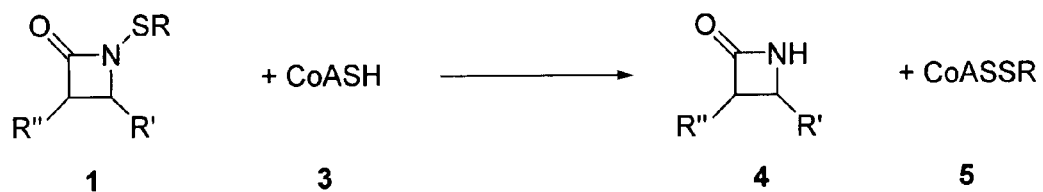
FIG. 79
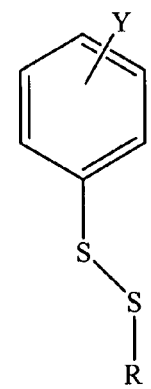
12
FIG. 80

22a-d a: R=Me
b: R=Et
c: R=i-Pr
d: R=s-Bu

23a-d a: R=Me
b: R=Et
c: R=i-Pr
d: R=s-Bu

24a,c a: R=Me
b: R=Et
c: R=i-Pr
d: R=s-Bu

25a,c a: R=Me
b: R=Et
c: R=i-Pr
d: R=s-Bu

26a a: R=Me
b: R=Et
c: R=i-Pr
d: R=s-Bu

45a
R = alkyl (methyl)

ASYMMETRIC DISULFIDES AND ARYL-ALKYL DISULFIDES AS ANTI-BACTERIAL AGENTS

CROSS-REFERENCE TO RELATED APPLICATION

The present application claims the benefit of U.S. Provisional Application Ser. No. 60/777,723 filed Feb. 27, 2006, which is hereby incorporated by reference herein in its entirety, including any figures, tables, nucleic acid sequences, amino acid sequences, and drawings.

GOVERNMENT SUPPORT

This invention was made with government support under National Institutes of Health grant number R01 AI 51351. The government has certain rights in the invention.

BACKGROUND OF THE INVENTION

The development of multi-drug resistant *Staphylococcus* infections is an increasing concern for the global health community. Infection caused by methicillin-resistant *Staphylococcus aureus* (MRSA) is becoming increasingly difficult to treat with conventional antibiotics, leading to a sharp rise in clinical complications.

The gram-positive microbe, *Bacillus anthracis*, is the etiologic agent of anthrax, a disease common to livestock but also considered to be a primary biological warfare and bioterrorism threat to humans worldwide. Humans can be infected by exposure to spores or to infected animals or their waste products. Prompt medical attention of anthrax infections is required, and typically effective, by treatment with penicillin G, doxycycline, or the quinolone ciprofloxacin. If untreated, death usually results within several days to a week. There is growing concern that *B. anthracis* is developing resistance to the common drugs that are used to treat the disease, and new antibiotics possessing a different mode of action are urgently needed.

The discovery of N-alkylthio β-lactams in the Turos group has opened a new pathway in the development of potent anti-infectives (Turos, E. et al. *Bioorg. Med. Chem.*, 2005, 13:6289-6308; Long, T. E. et al. *Bioorg. Med. Chem.*, 2003, 11:1859-1863; Turos, E. et al. *Bioorg. Med. Chem. Lett.*, 2002, 12:2229-2231). While the initial results have been exciting, much of their mode of action remains to be completely understood.

Long ("N-thiolated β-lactams: Chemistry and biology of a novel class of antimicrobial agents for MRSA" University of South Florida Dissertation, 2003) and Heldreth ("N-thiolated beta-lactams: Chemistry, SAR and intracellular target of a novel class of antimicrobial and anticancer agents" University of South Florida Dissertation, 2004) were able to show that a disulfide-forming thiol transfer to intracellular thiols such as coenzyme A or glutathione was a key metabolic pathway for this class of compounds. Further, it was demonstrated that these drugs are most effective in those strains of bacteria where coenzyme A is present in high concentrations relative to other cytosolic thiols (Long, T. "N-thiolated β-lactams: Chemistry and biology of a novel class of antimicrobial agents for MRSA" University of South Florida Dissertation, 2003; Newton, G. L. et al. *J. Bacteriology*, 1996, 178(7): 1990-1995), and, thus, where mixed CoA disulfides are produced within the cells (see scheme of thiol transfer from β-lactam to CoA in FIG. 1A).

Although the abundance of CoA in *Staphylococcus* and *Bacillus* stems from its role within the thiol-redox buffer of these strains (Kaleidagraph, version 3.5.1.0, available from Synergy Software), the thiol-redox buffer is not directly affected by reaction of the N-alkylthio β-lactams with CoA. Although CoA disulfide reductase was ruled out as an enzymatic target, at least one of the two key mechanistic postulates is likely still valid:

1.) The CoA mixed disulfide produced by reaction of CoA with the N-alkylthio β-lactams acts as an inhibitor of a CoA-selective enzyme.

2.) The N-alkylthio β-lactams are actually the active molecules, and the thiol-transfer reaction of CoA functions as a natural defense mechanism.

If postulate (1) is correct, it stands to reason that a large number of enzymatic pathways may be affected, since CoA is reported to be involved with approximately four percent of all known enzymatic reactions (Lee, C-H. and Chen, A. F. "Immobilized coenzymes and derivatives" in *The Pyridine Nucleotide Coenzymes*, Everse, J. et al. Eds, New York: Academic Press, 1982). Nonetheless, the elucidation of individual pathways is important to the further development of these valuable compounds.

N-Alkylthio β-lactams and Fatty Acid Synthesis

Recent experiments conducted by Dr. Seyoung Jang of the Turos group demonstrated that treatment of *S. aureus* with lactam 8 (FIG. 2) greatly reduced uptake of radiolabeled acetate (as shown by the graph in FIG. 3) (Leonardi, R. et al. *J. Biol. Chem.*, 2005, 280:3314-3322; Slater-Radosti, C. et al. *Antimicrobial Chemother.*, 2001, 48:1-6; Higgins, D. L. et al. *Antimicro. Agents Chemother.*, 2005, 49(3):1127-1134; Bligh, E. G. and Dyer, W. J. *Can. J. Biochem. Phys.*, 1959, 37:911-197). This reduction in uptake suggests that a key mechanistic pathway of the N-alkylthio β-lactams is the inhibition of fatty acid synthesis.

Bacterial fatty acid synthesis, often called Type II FAS, has been a target for antibiotics development for nearly a decade (Marrakchi, H. et al. *Biochem. Sco. Trans.*, 2002, 30(6):1050-1055; Campbell, J. W. and Cronan, J. E. *Ann. Rev. Microbiol.*, 2001, 55:305-352; Cronan, J. E., Jr. and Rock, C. O. in *E. Coli and Salmonella typhimurium: Cellular and Molecular Biology* (Neidhardt, F. C. et al. Eds.), Washington, D.C.: American Society for Microbiology, 1996; Rock, C. O. and Cronan, J. E., Jr. *Biochim. Biophys. Acta.*, 1996, 1302:1-16; Heath, R. J. and Rock, C. O. *J. Biol. Chem.*, 1996, 271(18):10996-11000; Daines, R. A. et al. *J. Med. Chem.*, 2003, 46:5-8; Jones, P. B. et al. *J. Med. Chem.*, 2000, 43:3304-3314; He, X. and Reynolds, K. A. *Antimicrob. Agents Chemother.*, 2002, 46(5):1310-1318; Jones, P. B. et al. *J. Med. Chem.*, 2000, 43:3304-3314; Nie, Z. et al. *J. Med. Chem.*, 2005, 48:1596-1609; He, X. et al. *Antimicro. Agents Chemother.*, 2004, 48:3093-3102; Choi, K-H. et al. *J. Bacteriology*, 2000, 182 (2):365-370). Unlike mammalian (Type I) FAS, which operates through a multienzyme complex (Voet, D. and Voet, G. *Biochemistry*, $3^{rd}$ *Ed.*, John Wiley and Sons: Hoboken, N.J., 2004), bacterial FAS utilizes a series of discreet enzymes. This key difference opens opportunities for the development of inhibitors which are selective for Type II FAS (Marrakchi, H. et al. *Biochem. Sco. Trans.*, 2002, 30(6):1050-1055).

Type II FAS is depicted in the scheme of FIG. 4 (Marrakchi, H. et al. *Biochem. Sco. Trans.*, 2002, 30(6):1050-1055; Voet, D. and Voet, G. *Biochemistry*, $3^{rd}$ *Ed.*, John Wiley and Sons: Hoboken, N.J., 2004). The synthetic cycle represents a recurring sequence of condensation (two-carbon elongation), reduction, dehydration, and reduction. Throughout the fatty acid cycle, the acyl substrates are carried from enzyme to enzyme by the acyl carrier protein (FIG. 5). This small protein contains a pantethine/thiol arm identical to that of CoA. Within this cycle, only two enzymes, malonyl/acetyl-CoA-ACP transacylase (MAT) and β-ketoacyl-ACP synthase III (FabH) utilize a CoA derivative.

Of the two possible enzymes, FabH seemed the logical first choice for exploration: first because of its role as the initial condensing enzyme in the FAS cascade, and secondly because FabH has already been purified from several species and its mode of action extensively studied (Marrakchi, H. et al. *Biochem. Sco. Trans.*, 2002, 30(6):1050-1055; He, X. and Reynolds, K. A. *Antimicrob. Agents Chemother.*, 2002, 46(5): 1310-1318; Qui, X. et al. *Protein Sci.*, 2005, 14:2087-2094; Davies, C. et al. *Structure*, 2000, 8:185-195; Scarsdale, J. N. et al. *J. Biol. Chem.*, 2001, 276(23):20516-20522; Li, Y. et al. *J. Bacteriol.*, 2004, 187:3795-3799).

The FabH active site contains a single cysteine residue located within a lipophilic pocket. Following binding of acetyl CoA, acetyl transfer from CoA to the active-site cysteine produces an S-acetyl cysteine and free CoA. Malonyl ACP then binds to the enzyme and undergoes a condensation reaction with the S-acetyl cysteine, with concurrent loss of $CO_2$. Elimination of the cysteine produces β-ketobutanoyl-ACP, which is carried into the rest of the fatty acid cycle (FIG. 6).

Based on this mechanism, the inhibition of FabH by a CoA mixed disulfide was visualized. It was hypothesized by the present inventors that this inhibition involves not only a non-covalent inhibition by occupation of the binding pocket, but also a potentially irreversible inhibition via transfer of the alkylthio moiety to the active site cysteine of the FabH enzyme (FIGS. 1A-1B).

In order to explore these possibilities, it was proposed that a set of CoA mixed disulfides be tested for inhibitory activity against FabH. And, since it was possible that the N-alkylthio β-lactams might interact directly with this enzyme, compounds 2a and 2g (FIGS. 7A and 7B, respectively) were also tested against FabH.

For the past decade, there has been considerable interest in the development of FabH inhibitors (Marrakchi, H. et al. *Biochem. Sco. Trans.*, 2002, 30(6):1050-1055; Campbell, J. W. and Cronan, J. E. *Ann. Rev. Microbiol.*, 2001, 55:305-352; Daines, R. A. et al. *J. Med. Chem.*, 2003, 46:5-8; Qui, X. et al., *Protein Science*, 2005, 14:2087-2094; Jones, P. B. et al. *J. Med. Chem.*, 2000, 43:3304-3314; He, X. and Reynolds, K. A. *Antimicrob. Agents Chemother.*, 2002, 46(5):1310-1318). The key role of this enzyme in Type II fatty acid synthesis, as well as the differences between bacterial and mammalian FAS, make FabH a desirable target for the inhibition of bacterial growth (Marrakchi, H. et al. *Biochem. Sco. Trans.*, 2002, 30(6):1050-1055; Campbell, J. W. and Cronan, J. E. *Ann. Rev. Microbiol.*, 2001, 55:305-352).

It has recently reported that compounds such as the N-alkylthio β-lactams (FIG. 7BA) (Turos, E. et al. *Bioorg. Med. Chem. Lett.*, 2002, 12:2229-2231; Turos, E. et al. *Tetrahedron*, 2000, 56:5571-5578; Turos, E. et al. *Bioorg. Med. Chem.*, 2005, 13:6289-6308; Coates, C. et al. *Bioorg. Med. Chem.*, 2003, 11:193-196; Long, T. E. et al. *Bioorg. Med. Chem.*, 2003, 11:1859-1863; Turos, E. et al. *Bioorg. Med. Chem. Lett.*, 2002, 12:2229-2231; Heldreth, B. et al. *Bioorg. and Med. Chem.*, 2006, 14:3775-3784) and N-alkylthio-2-oxazolidinones (FIG. 7BB) (Mishra, R. K. et al. *Bioorg. Med. Chem. Lett.*, 2006, 16(8):2081-2083) are able to inhibit the proliferation of methicillin-resistant *Staphylococcus aureus* (MRSA) and *Bacillus anthracis*. A major pathway for this inhibition involves thiol-transfer to Coenzyme A to produce an alkyl-CoA mixed disulfide (5 in the scheme of FIG. 79). Experimental evidence suggests that the resulting aryl-alkyl disulfide may inhibit FabH (6 in the scheme of FIG. 79) by reversibly "capping" the active site cysteine through a thiol-disulfide exchange (FIG. 79) (Revell, K. D. et al. *Bioorg. and Med. Chem*, 2007, 15(6):2453-2467).

In light of this, the semi-irreversible inhibition of FabH by CoA/alkyl mixed disulfides opens a new strategy for the blocking of this important enzyme.

Although alkyl-CoA disulfides have been shown to bind tightly to purified FabH, treatment of *S. aureus* cultures with these disulfides does not inhibit bacterial growth, likely because the multicharged CoA cannot easily traverse the cell membrane (Clarke, K. M. et al. *J. Am. Chem. Soc.*, 2005, 237:11234-11235). However, it was postulated that smaller, non-ionic disulfides might be able to function as CoA disulfide mimics: they could block the FabH active site via thiol transfer in the same manner as the CoA mixed disulfides, but their smaller size and greater lipophilicity make it easier for them to enter the cell and inhibit FabH. To evaluate this hypothesis, a set of simple disulfides was prepared, and their activities against several bacteria were tested.

The design of CoA mixed-disulfide mimics was aided by previous research into FabH inhibitors. Jones et al. (Johns Hopkins University) reported that compound 30 (FIG. 8B) showed good activity against *M. tuberculosis*, presumably through inhibition of FabH (He, X. and Reynolds, K. A. *Antimicrob. Agents Chemother.*, 2002, 46(5):1310-1318). Kevin Reynolds (Portland State) reported compound 31 (FIG. 8C) inhibits *E. coli* FabH. Researchers at GlaxoSmithKline recently published data on a class of FabH inhibitors, including the crystal structure of *S. aureus* FabH (Daines, R. A. et al. *J. Med. Chem.*, 2003, 46:5-8), and the co-crystal structure of compound 29 (FIG. 8A, where R=$(CH_2)_4CO_2H$) in *E. coli* FabH (Qui, X. et al. *Protein Science*, 2005, 14:2087-2094).

The crystal structures reported for compound 29 (Qui, X. et al. *Protein Sci.*, 2005, 14:2087-2094) indicate that the active site is located within a fairly deep, lipophilic "pocket" into which acyl-CoA or acyl-ACP are able to stretch their lipophilic arm. Further, the co-crystal data reveals that, in the binding mode of compound 29, the 2,6-dichlorophenyl moiety reaches into the active site, such that the 4-position of the phenyl ring is proximal to the active site cysteine. Based on this, it was postulated that a molecule such as 32 (FIG. 9) might be able to effectively undergo thiol-disulfide exchange with the active site cysteine of FabH.

The present inventors postulated that, unlike noncovalent inhibitors, CoA disulfide mimics would not require long residence times in the active site. Rather, they need only to be able to enter the site and transfer the thiol. With this goal in mind, and in light of the efficacy of the nonpolar compounds 30 and 31, it was postulated that small, somewhat lipophilic disulfides of the general type (FIG. 80) would be best suited to access the pocket.

However, a deeper analysis suggests that compound 32 may be more specific than necessary. The effectiveness of benchmark compound 29 stems from its residence time in FabH. That is, its rate of binding to FabH is very fast, while its rate of dissociation is relatively slow.

In the case of a CoA mixed disulfide mimic, however, such long residence times may not be needed. Rather, it is critical that the disulfides be small enough to fit easily into the active-site pocket to transfer the thiol to the cysteine. To test this hypothesis, a set of very simple aryl-alkyl disulfides (FIGS. 10 and 11) were prepared by semicombinatorial methods and analyzed for activity against *S. aureus*, *B. anthracis*, and *Escherichia coli*.

BRIEF SUMMARY OF THE INVENTION

The present invention concerns N-alkylthio β-lactams and disulfide compounds (e.g., aryl-alkyl disulfides), and methods for their use as anti-bacterial compounds. The N-alkylthio β-lactams do not function like the classical β-lactams nor show similar structure-activity relationships (SAR). An investigation of their mode-of-action is described herein. As shown in FIGS. 1A-B, N-alkylthio β-lactams (FIG. 1A) function as prodrugs to produce mixed CoA disulfides in the cell (FIG. 1B), which inhibit FabH by "capping" the active site cysteine (see Table 1). A crystal structure of *E. coli* FabH after treatment with CoASSMe shows that the SMe is covalently bound to the active site cysteine. Covalent FabH inhibition is not reversed by dialysis but is reversed by addition of dithiothreitol (DTT). These results suggest that N-alkylthio β-lactams can be used as anti-bacterial agents, such as anti-*Staphylococcus aureus* (e.g., methicillin-resistant *S. aureus* (MRSA)) agents and anti-*Bacillus anthracis* (anthrax) agents.

The present invention also concerns the use of asymmetric disulfides comprising or consisting of coenzyme A on one side of the disulfide, and an alkyl chain on the other side of the disulfide, as treatments and preventatives for bacterial infection. It has been found that these molecules, which may be synthesized in the laboratory or produced within the bacterial cell through the action of a thiol-transfer agent such as the N-alkylthio β-lactam antibodies, act as potent antibacterial compounds effective against several genera, most notably *Bacillus* spp. and *Staphylococcus* spp., including MRSA, if produced or delivered intracellularly. These compounds function as potent inhibitors of type II fatty acid synthesis through the inhibition of a key condensing enzyme, FabH. This inhibition takes place through a mechanism involving a thiol-disulfide exchange to cap the active-site cysteine of FabH through formation of a disulfide.

The present invention further includes the use of small aryl-alkyl disulfides, which act as molecular mimics of the asymmetric coenzyme A disulfides described above, and which also cap FabH through a thiol-disulfide exchange. Unlike the coenzyme A disulfides, these disulfides do not need to be produced inside the cell, or delivered to the interior of the cell, to be effective against *Bacillus* and *Staphylococcus*. A series of small aryl-alkyl disulfides was prepared and tested against methicillin-resistant *Staphylococcus aureus* (MRSA) and *Bacillus anthracis*. Several of these compounds inhibited MRSA at micromolar and *B. anthracis* at nanomolar concentrations.

In one aspect, the present invention includes the N-alkylthio β-lactams and disulfide compounds (e.g., alkyl-coenzyme A asymmetric disulfides or aryl-alkyl disulfides) described herein, or pharmaceutically acceptable salts thereof, which are useful as anti-bacterial agents. In another aspect, the present invention includes compositions comprising one or more N-alkylthio β-lactams and/or disulfide compounds (e.g., alkyl-coenzyme A asymmetric disulfides or aryl-alkyl disulfides), and a pharmaceutically acceptable carrier. In another aspect, the present invention includes methods for treating or preventing (e.g., delaying onset of) bacterial infection by administering an effective amount of an N-alkylthio β-lactam or disulfide compound (e.g., alkyl-coenzyme A asymmetric disulfides or aryl-alkyl disulfides) to a human or non-human patient in need thereof.

Numbers in bold and/or in parenthesis refer to specific compounds described herein.

The anti-bacterial compounds of the present invention act against several infective agents, and most notably *Bacillus* spp. and *Staphylococcus* spp., including MRSA.

BRIEF DESCRIPTION OF THE FIGURES

FIGS. 8A-8C show compounds 29, 30, and 31, which are reported to show antibacterial activity (compound 30) or inhibit FabH (compounds 29, 31).

FIG. 10 shows a scheme for the synthesis of aryl-alkyl disulfides.

FIGS. 11A-J show the chemical structures of starting thiols (ArSH, scheme of FIG. 10) for aryl-alkyl disulfides 33-45, respectively.

FIGS. 14A-B show the synthesis schemes of second-round disulfides.

FIGS. 15A-B show disulfides 38c and 38d, respectively.

FIG. 28 shows the chemical structure of compound 28a.

FIG. 34 shows the chemical structure of compound 33a.
FIG. 45 shows the chemical structure of compound 35a.
FIG. 51 shows the chemical structure of compound 36a.
FIG. 52 shows the chemical structure of compound 38a.

FIG. 57 shows the chemical structure of compound 41a.
FIG. 58 shows the chemical structure of compound 42a.
FIG. 64 shows the chemical structure of compound 43a.
FIG. 68 shows the chemical structure of compound 44a.
FIG. 72 shows the chemical structure of compound 46a.

FIG. 73A) prepared and tested against FabH, and the reaction in which the alkylthio moiety is transferred from the lactam to the thiol group of coenzyme A, forming a mixed CoA-alkyl disulfide (FIG. 73B), as shown S. aureus lysate treated with N-alkylthio β-lactams.

FIG. 75 shows the chemical structure of a disulfide compound of the invention. A, B=electron withdrawing groups (such as acyl, nitro, sulfonyl, amido, imino, etc.). R=H, alkyl, cycloalkyl, alkoxy, aryl, heteroaryl, heteroalkyl, alkanoyl, 2-aminoalkyl, 2-hydroxyalkyl, and halo; preferably, alkyl (such as methyl, ethyl, isopropyl, sec-butyl, n-propyl, n-butyl, etc.).

FIGS. 76A-76B show the chemical structures of disulfide compounds of the invention. In FIGS. 76A-B, A, B=electron withdrawing groups (such as acyl, nitro, sulfonyl, amido, imino, etc.). In FIGS. 76A-B, R=H, alkyl, cycloalkyl, alkoxy, aryl, heteroaryl, heteroalkyl, alkanoyl, 2-aminoalkyl, 2-hydroxyalkyl, and halo; preferably, alkyl (such as methyl, ethyl, isopropyl, sec-butyl, n-propyl, n-butyl, etc.). In FIG. 76A, Y=C, N, or O (and may be the same or different). In FIG. 76B, Y=C, N, O, or S (and may be the same or different).

FIG. 77 shows the chemical structure of small aryl-alkyl disulfides of the invention. X=electron withdrawing groups (such as acyl, nitro, sulfonyl, amido, imino, etc.) R=H, alkyl, cycloalkyl, alkoxy, aryl, heteroaryl, heteroalkyl, alkanoyl, 2-aminoalkyl, 2-hydroxyalkyl, and halo; preferably, alkyl (such as methyl, ethyl, isopropyl, sec-butyl, n-propyl, n-butyl, etc.).

FIGS. 78A-78B show compounds (N-alkylthio beta lactams and N-alkylthio-2-oxazolidinones, respectively) which inhibit the growth of MRSA and B. anthracis via thiol transfer to CoA. In FIGS. 78A-78B, R is selected from the group consisting of H, alkyl, aryl, and cycloalkyl, R' is H, alkyl or acyl, and R" is selected from the group consisting of H, alkyl, aryl, and heteroalkyl.

FIG. 79 shows a pathway for inhibition of MRSA and Bacillus anthracis proliferation, involving thiol transfer to Coenzyme A to produce an alkyl-CA mixed disulfide. Experimental evidence suggests that the resulting aryl-alkyl disulfide may inhibit FabH by reversibly "capping" the active site cysteine through a thiol-disulfide exchange.

FIG. 80 shows CoA-disulfide mimics of the invention. Y=electron withdrawing groups (such as acyl, nitro, sulfonyl, amido, imino, etc.). R=H, alkyl, cycloalkyl, alkoxy, aryl, heteroaryl, heteroalkyl, alkanoyl, 2-aminoalkyl, 2-hydroxyalkyl, and halo; preferably, alkyl (such as methyl, ethyl, isopropyl, sec-butyl, n-propyl, n-butyl, etc.).

DETAILED DESCRIPTION OF THE INVENTION

Figure 1:
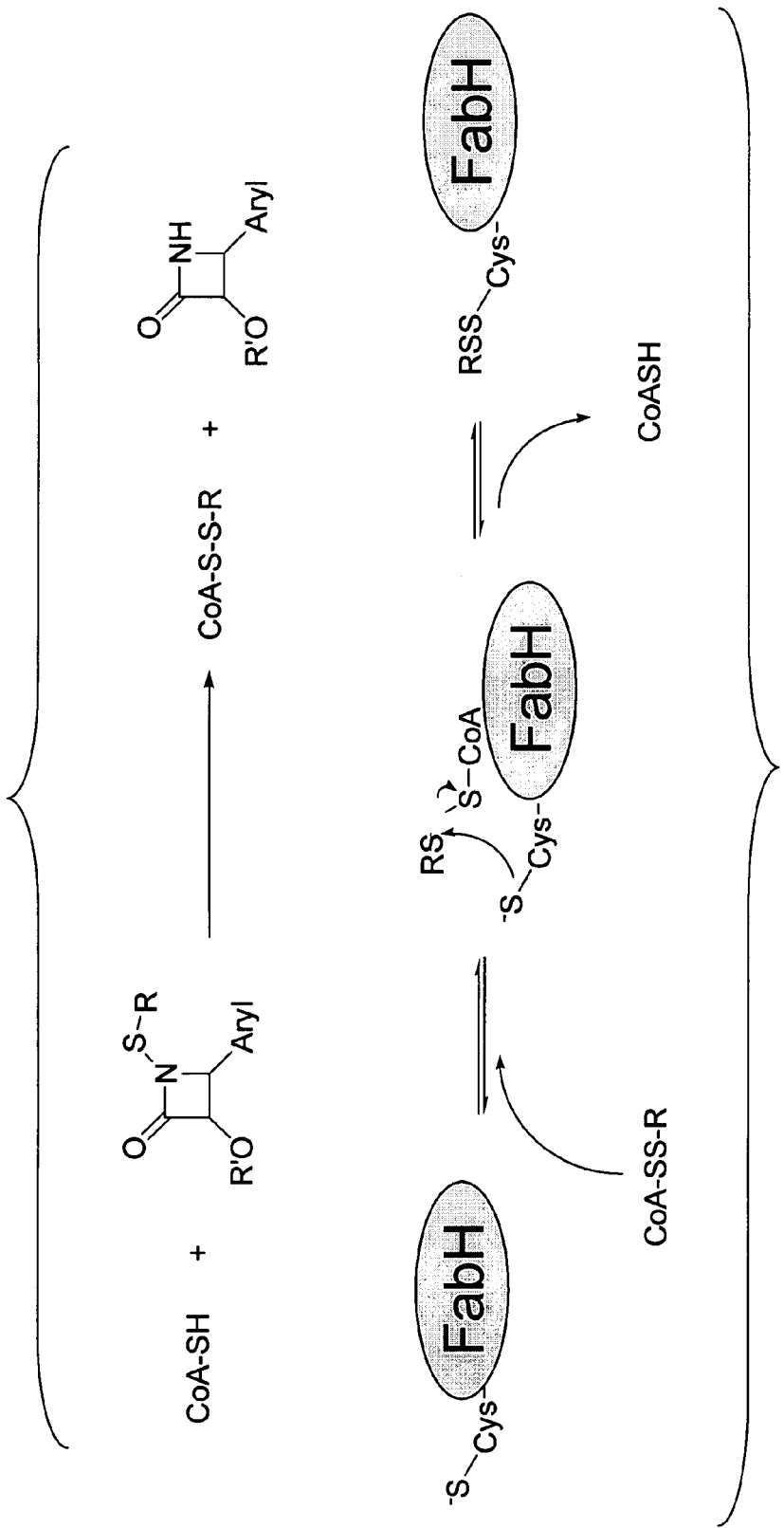
FIGS. 1A-1B show a scheme of thiol transfer from β-lactam to CoA. The proposed mechanism involves capping of the active-site thiol in the FabH protein.
Figure 2:
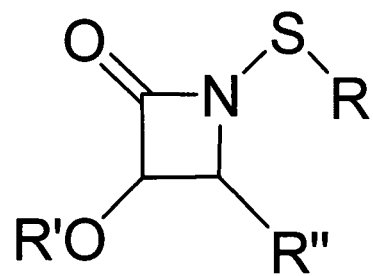
FIG. 2 shows the general structure of the N-alkylthio β-lactam, also referred to herein as compound 8 or lactam 8 in which R and R' are methyl, and R" is aryl. N-alkylthio β-lactams, which do not function like the classical β-lactams, nor show similar structure-activity relationships (SAR), are antibiotically active against *Staphylococcus, Bacillus, Micrococcus, Streptococcus, Neisseria, Streptomyces, Mycobacterium tuberculosis* (*Bioorg. Med. Chem.*, 2005, 13:62e89-6308; *Bioorg. Med. Chem.*, 2003, 11:193-196; *Bioorg. Med. Chem.*, 2003, 11:1859-1863; and *Bioorg Med. Chem. Lett.*, 2002, 12:2229-2231).
Figure 3:
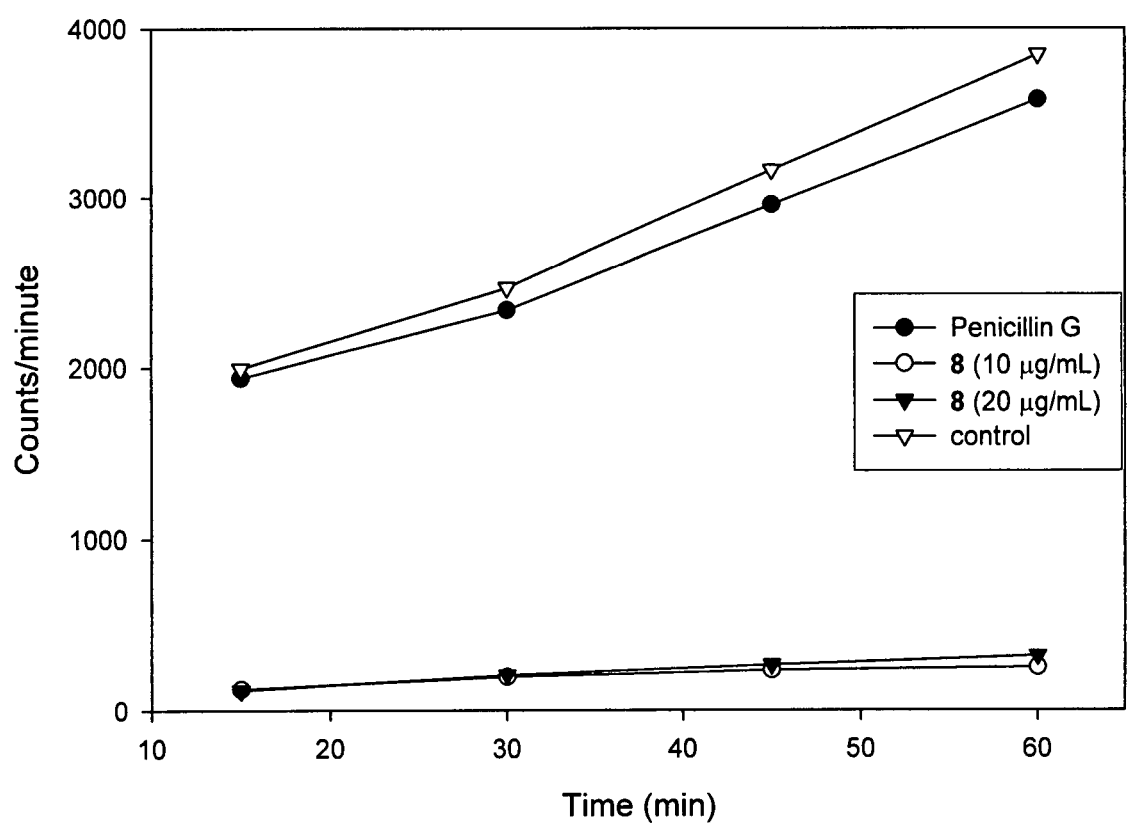
FIG. 3 shows inhibition of fatty acid synthesis by N-alkylthio β-lactam 8 as determined by measurement of uptake of radiolabeled $^3$H acetate. Incidence of Radiation (CPM) versus time for *S. aureus* treated with: a. Pen G (2 μg/mL, 2×MIC), b. Compound 8 (20 μg/mL, 2×MIC), c. Compound 8 (10 μg/mL, 1×MIC); d. control in the presence of $^3$H acetate.
Figure 4:
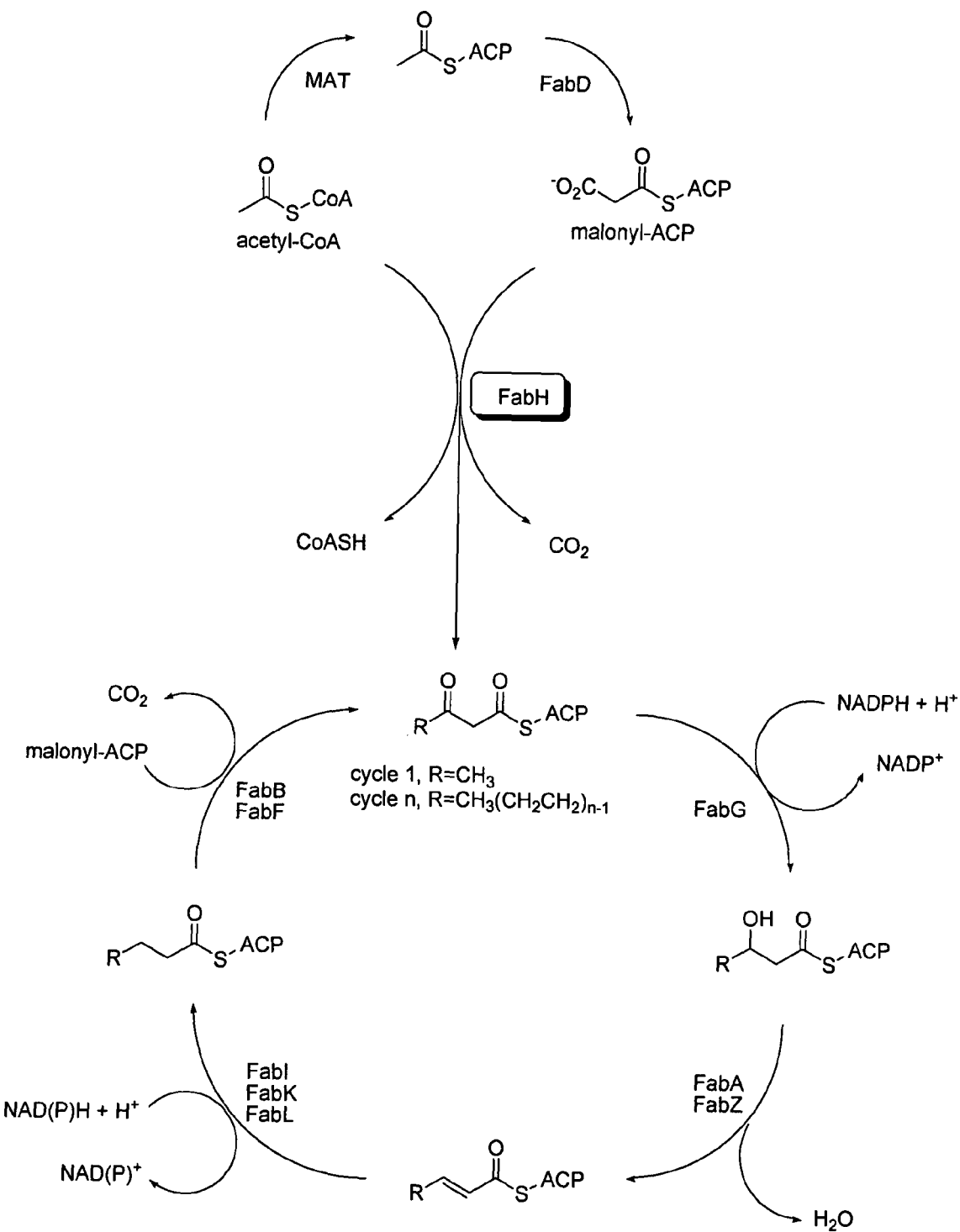
FIG. 4 shows type II fatty acid synthesis (FAS).
Figure 5:
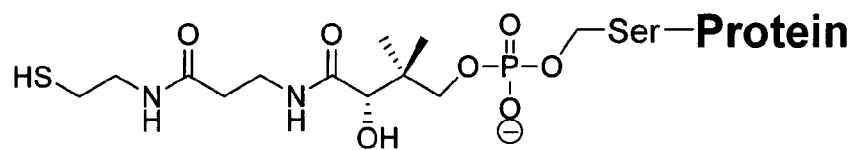
FIG. 5 shows the chemical structure of acyl carrier protein.
Figure 6:
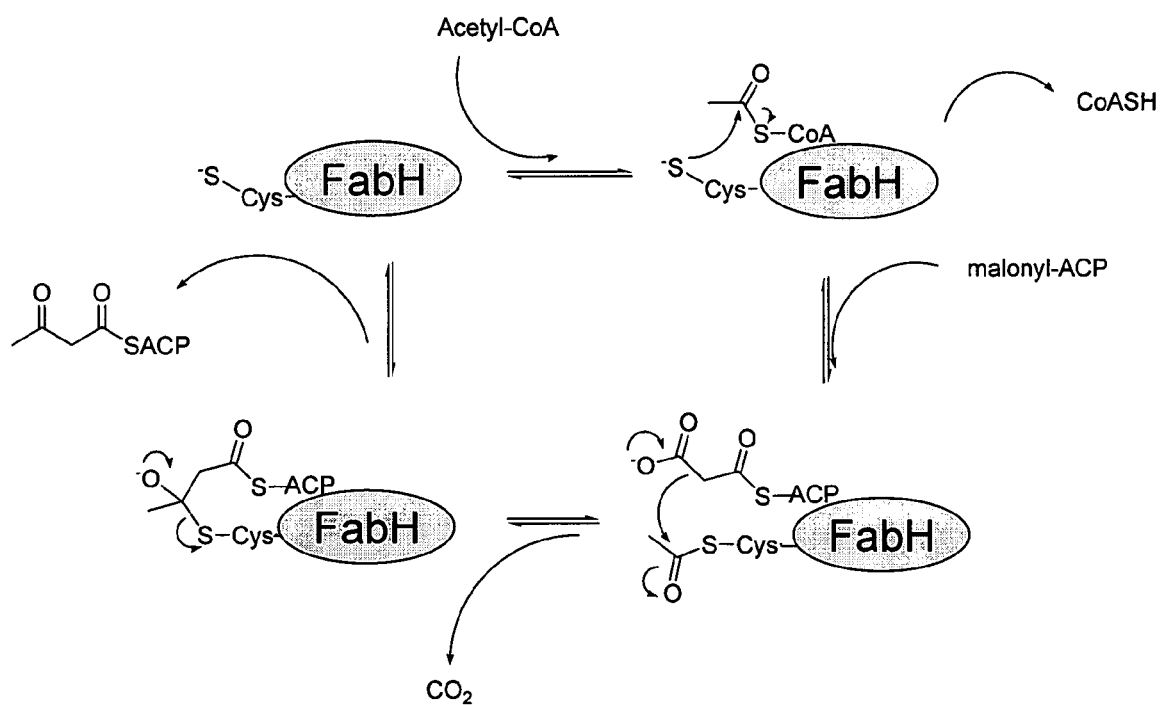
FIG. 6 shows the mechanism of FabH. Elimination of the cysteine produces β-ketobutanoyl-ACP, which is carried into the rest of the fatty acid cycle.

In one aspect, the invention comprises compound having a chemical structure selected from the group consisting of 25a-f, 26b, 26c, 28a-c, 32,33a-f, 34b, 34c, 38a-f, 39a, 41a, 42a-d, 43a-d, 44a-d, 45a, 46a, 47, 48, 49, 50, 51, 52, 53, and 54, or a pharmaceutically acceptable salt thereof, wherein R and R' are the same or different, each being independently selected from the group consisting of H, alkyl, cycloalkyl, alkoxy, aryl, heteroaryl, heteroalkyl, alkanoyl, 2-aminoalkyl, 2-hydroxyalkyl, and halo.

In another embodiment, the compound of the invention has the chemical structure I (FIG. 75), or a pharmaceutically acceptable salt thereof, wherein A and B are each electron withdrawing groups and are the same or different, and wherein R is selected from the group consisting of H, alkyl, cycloalkyl, alkoxy, aryl, heteroaryl, heteroalkyl, alkanoyl, 2-aminoalkyl, 2-hydroxyalkyl, and halo. Preferably, A and B are each independently selected from the group consisting of acyl, nitro, sulfonyl, amido, and imino.

In another embodiment, the compound of the invention has the chemical structure II (FIG. 76A), or a pharmaceutically acceptable salt thereof, wherein A and B are each electron withdrawing groups, wherein Y is the same or different and is independently selected from the group consisting of carbon, nitrogen, and oxygen, and wherein R is selected from the group consisting of H, alkyl, cycloalkyl, alkoxy, aryl, heteroaryl, heteroalkyl, alkanoyl, 2-aminoalkyl, 2-hydroxyalkyl, and halo. Preferably, A and B are each independently selected from the group consisting of acyl, nitro, sulfonyl, and amido, and imino.

In another embodiment, the compound of the invention has the chemical structure III (FIG. 76B), or a pharmaceutically acceptable salt thereof, wherein A and B are each electron withdrawing groups, wherein Y is the same or different and is independently selected from the group consisting of carbon, nitrogen, oxygen, and sulfur, and wherein R is selected from the group consisting of H, alkyl, cycloalkyl, alkoxy, aryl, heteroaryl, heteroalkyl, alkanoyl, 2-aminoalkyl, 2-hydroxyalkyl, and halo. Preferably, A and B are each independently selected from the group consisting of acyl, nitro, sulfonyl, and amido, and imino.

In another embodiment, the compound of the invention has the chemical structure of any of the compounds of FIGS. 77-79, 81, and 82-86, or pharmaceutically acceptable salts thereof.

In another aspect, the invention comprises a composition comprising a compound of the invention (e.g., an alkyl-coenzyme A asymmetric disulfide or aryl-alkyl disulfide), and a pharmaceutically acceptable carrier. In another embodiment, the composition comprises a compound of structures I, II, and/or III, or a pharmaceutically acceptable salt thereof, and pharmaceutically acceptable carrier.

In one embodiment, the composition further comprises an additional antibiotic agent. Optionally, the aforementioned compositions are formulated for feeding to livestock.

In another aspect, the invention comprises a method for treating or preventing a bacterial infection, comprising administering to a subject in need thereof an effective amount of a compound comprising an alkyl-coenzyme A asymmetric disulfide or aryl-alkyl disulfide. Preferably, the bacteria is selected from the group consisting of *Staphylococcus, Bacillus, Micrococcus, Streptococcus, Neisseria, Streptomyces*, and *Mycobacterium tuberculosis*. In another preferred embodiment, the bacteria is methicillin-susceptible *Staphylococcus aureus*, methicillin-resistant *Staphylococcus aureus* (MSSA or MRSA), *Bacillus anthracis*, or *Escherichia coli*. Preferably, the compound of the invention is administered by a route selected from the group consisting of oral, intravenous, and topical.

In another embodiment of the invention, the compound has the chemical structure I (FIG. 75), or a pharmaceutically acceptable salt thereof, wherein A and B are each electron withdrawing groups and are the same or different, and wherein R is selected from the group consisting of H, alkyl, cycloalkyl, alkoxy, aryl, heteroaryl, heteroalkyl, alkanoyl, 2-aminoalkyl, 2-hydroxyalkyl, and halo. Preferably, A and B are each independently selected from the group consisting of acyl, nitro, sulfonyl, amido, and imino.

In another embodiment of the invention, the compound has the chemical structure II (FIG. 76A), or a pharmaceutically acceptable salt thereof, wherein A and B are each electron withdrawing groups, wherein Y is the same or different and is independently selected from the group consisting of carbon, nitrogen, and oxygen, and wherein R is selected from the group consisting of H, alkyl, cycloalkyl, alkoxy, aryl, heteroaryl, heteroalkyl, alkanoyl, 2-aminoalkyl, 2-hydroxyalkyl, and halo. Preferably, A and B are each independently selected from the group consisting of acyl, nitro, sulfonyl, and amido, and imino.

In another embodiment of the invention, the compound has the chemical structure III (FIG. 76B), or a pharmaceutically acceptable salt thereof, wherein A and B are each electron withdrawing groups, wherein Y is the same or different and is independently selected from the group consisting of carbon, nitrogen, oxygen, and sulfur, and wherein R is selected from the group consisting of H, alkyl, cycloalkyl, alkoxy, aryl, heteroaryl, heteroalkyl, alkanoyl, 2-aminoalkyl, 2-hydroxyalkyl, and halo. Preferably, A and B are each independently selected from the group consisting of acyl, nitro, sulfonyl, and amido, and imino.

In another embodiment the compound is a nitrophenyl disulfide.

In another embodiment, the compound is a p- or m-nitrophenyl alkyl disulfide.

In another embodiment, the compound is a methyl disulfide and the bacteria is *Escherichia coli*.

In another embodiment, the compound is an isopropyl- or s-disulfide, and the bacteria is *Staphylococcus* or *Bacillus*.

In another embodiment, the compound is an alkyl disulfide, and the bacteria is *Mycobacterium tuberculosis*.

In another embodiment, the compound is selected from the group consisting of 25a-f, 26b, 26c, 28a-c, 32,33a-f, 34b, 34c, 38a-f, 39a, 41a, 42a-d, 43a-d, 44a-d, 45a, 46a, 47, 48, 49, 50, 51, 52, 53, and 54, or a pharmaceutically acceptable salt thereof, wherein R and R' are the same or different, each being independently selected from the group consisting of H, alkyl, cycloalkyl, alkoxy, aryl, heteroaryl, heteroalkyl, alkanoyl, 2-aminoalkyl, 2-hydroxyalkyl, and halo.

In another embodiment, both an alkyl-coenzyme A asymmetric disulfide and an aryl-alkyl disulfide are administered.

In another embodiment, the compound has the chemical structure of any of the compounds of FIGS. 77-79, 81, and 82-86, or pharmaceutically acceptable salts thereof.

In another aspect, the invention comprises a method for inhibiting the growth of bacteria, comprising contacting the bacteria with an effective amount of a compound comprising an alkyl-coenzyme A asymmetric disulfide or aryl-alkyl disulfide; or applying the compound to a surface that may come in contact with the bacteria. Preferably, the bacteria is selected from the group consisting of *Staphylococcus, Bacillus, Micrococcus, Streptococcus, Neisseria, Streptomyces*, and *Mycobacterium tuberculosis*. In one embodiment, the bacteria is methicillin-susceptible *Staphylococcus aureus* or methicillin-resistant *Staphylococcus aureus* (MSSA or MRSA). In one embodiment, the bacteria is *Bacillus anthracis*. In another embodiment, the bacteria is *Escherichia coli*. In one embodiment, the compound is a nitrophenyl disulfide. In another embodiment, the compound is a p- or m-nitrophenyl alkyl disulfide. In another embodiment, the compound is a methyl disulfide and the bacteria is *Escherichia coli*. In another embodiment, the compound is an isopropyl- or s-disulfide, and the bacteria is *Staphylococcus* or *Bacillus*. In another embodiment, the compound is an alkyl disulfide, and the bacteria is *Mycobacterium tuberculosis*.

Preferably, in the bacterial growth inhibiting method of the invention, the compound has the chemical structure I, or a pharmaceutically acceptable salt thereof, wherein A and B are each electron withdrawing groups and are the same or different, and wherein R is selected from the group consisting of H, alkyl, cycloalkyl, alkoxy, aryl, heteroaryl, heteroalkyl, alkanoyl, 2-aminoalkyl, 2-hydroxyalkyl, and halo. Preferably, A and B are each independently selected from the group consisting of acyl, nitro, sulfonyl, amido, and imino.

In another embodiment of the bacterial growth inhibiting method of the invention, the compound has the chemical structure II, or a pharmaceutically acceptable salt thereof, wherein A and B are each electron withdrawing groups, wherein Y is the same or different and is independently selected from the group consisting of carbon, nitrogen, and oxygen, and wherein R is selected from the group consisting of H, alkyl, cycloalkyl, alkoxy, aryl, heteroaryl, heteroalkyl, alkanoyl, 2-aminoalkyl, 2-hydroxyalkyl, and halo. Preferably, A and B are each independently selected from the group consisting of acyl, nitro, sulfonyl, and amido, and imino.

In another embodiment of the bacterial growth inhibiting method of the invention, the compound has the chemical structure III, or a pharmaceutically acceptable salt thereof, wherein A and B are each electron withdrawing groups, wherein Y is the same or different and is independently selected from the group consisting of carbon, nitrogen, oxygen, and sulfur, and wherein R is selected from the group consisting of H, alkyl, cycloalkyl, alkoxy, aryl, heteroaryl, heteroalkyl, alkanoyl, 2-aminoalkyl, 2-hydroxyalkyl, and halo. Preferably, A and B are each independently selected from the group consisting of acyl, nitro, sulfonyl, and amido, and imino.

In another embodiment of the bacterial growth inhibiting method of the invention, the compound is selected from the group consisting of 25a-f, 26b, 26c, 28a-c, 32,33a-f, 34b, 34c, 38a-f, 39a, 41a, 42a-d, 43a-d, 44a-d, 45a, 46a, 47, 48, 49, 50, 51, 52, 53, and 54, or a pharmaceutically acceptable salt thereof, wherein R and R' are the same or different, each being independently selected from the group consisting of H, alkyl, cycloalkyl, alkoxy, aryl, heteroaryl, heteroalkyl, alkanoyl, 2-aminoalkyl, 2-hydroxyalkyl, and halo. In one embodiment, both an alkyl-coenzyme A asymmetric disulfide and an aryl-alkyl disulfide are contacted or applied.

In another embodiment of the bacterial growth inhibiting method of the invention, the compound of the invention has the chemical structure of any of the compounds of FIGS. 77-79, 81, and 82-86, or pharmaceutically acceptable salts thereof.

In another aspect, the invention comprises an alkyl-coenzyme A asymmetric disulfide or aryl-alkyl disulfide of the invention, and instructions for treating an infection.

In another aspect, the invention comprises a method for treating or preventing a *Bacillus anthracis* infection, comprising administering to a subject in need thereof an effective amount of an N-alkylthio beta-lactam. In embodiment, the N-alkylthio beta-lactam has the chemical structure of compound 8, or a pharmaceutically acceptable salt thereof, wherein R is selected from the group consisting of H, alkyl, aryl, and cycloalkyl, wherein R' is H, alkyl or acyl, and wherein R" is selected from the group consisting of H, alkyl, aryl, and heteroalkyl. In another embodiment, the N-alkylthio beta-lactam is compound 2a or 2g, or a pharmaceutically acceptable salt thereof.

In another aspect, the invention comprises a method for inhibiting the growth of *Bacillus anthracis*, comprising contacting the *B. anthracis* with an effective amount of an N-alkylthio beta-lactam; or applying the N-alkylthio beta-lactam to a surface that may come in contact with the *B. anthracis*. Preferably, the N-alkylthio beta-lactam has the chemical structure of compound 8, or a pharmaceutically acceptable salt thereof, wherein R is selected from the group consisting of H, alkyl, aryl, and cycloalkyl, wherein R' is H, alkyl, or acyl, and wherein R" is selected from the group consisting of H, alkyl, aryl, and heteroalkyl. In one embodiment, the N-alkylthio beta-lactam is compound 2a or 2g, or a pharmaceutically acceptable salt thereof.

Mixed CoA disulfides (25a-f; FIG. 12) were prepared in good yields and high purity by treatment of free CoA (27) with stoichiometric amounts of the corresponding alkyl methanethiolsulfonates (Swerdlow, R. D. and Setlow, P. *J. Bact.,* 1983, 153(1):475-484).

In order to obtain FabH, Professor Kevin Reynolds (Portland State University), who reported the purification of FabH from *S. aureus* was contacted (He, X. and Reynolds, K. A. *Antimicrob. Agents Chemother.,* 2002, 46(5):1310-1318). Serendipitously, Professor Reynolds had been developing FabH inhibitors for *M. tuberculosis* (Scarsdale, J. N. et al. *J. Biol. Chem.,* 2001, 276(23):20516-20522; Li, Y. et al. *J. Bacteriol.,* 2004, 187:3795-3799). The Reynolds group prepared and tested 25c against FabH isolated from *E. coli* and *M. tuberculosis*. Results from these tests are shown in Table 1.

TABLE 1

$IC_{50}$(μM) for Alkyl-CoA disulfides 25a, and 25c-f against FabH derived from *E. coli* (ecFabH) and *M. tuberculosis* (mtFabH)

| CoASSR | R | ecFabH | mtFabH |
|---|---|---|---|
| 25a | methyl | 57.07 ± 4.48 | >300 |
| 25c | s-butyl | >300 | >300 |
| 25d | n-butyl | >300 | >300 |
| 25e | n-octyl | >300 | 23.2 ± 4.6 |
| 25f | n-decyl | >300 | 2.6 ± 1.6 |

The $IC_{50}$ (concentration of inhibitor at which 50% inhibition of ecFabH is achieved) was determined by duplicate assays with a minimum of six concentrations of inhibitor. The $IC_{50}$ values were calculated with Grafit 4.012 (Middlesex, United Kingdom).

This data indicates that CoA disulfides can, in fact, inhibit FabH. However, it also suggests that the optimal size of the alkylthio piece for FabH inhibition is dependent on the strain of bacteria from which it comes. The FabH from *E. coli* is most susceptible to a small alkylthio fragment, while the *M. tuberculosis* FabH is more effectively inhibited by a long-chain variant. Based on the propensity of *S. aureus* to produce branched-chain fatty acids (Qui, X. et al. *Protein Sci.,* 2005, 14:2087-2094), it is postulated that the branched alkyl chains may be optimal for inhibiting *S. aureus* FabH. This postulate is consistent with the observation that N-sec-butylthio β-lactams such as 2g are the most potent N-alkylthio analogs against both MSSA and MRSA (Turos, E. et al. *Bioorg. Med. Chem. Lett.,* 2002, 12:2229-2231).

Reynolds also reported that the X-ray crystal structure of *E. coli* FabH which had been pretreated with 25a shows a methylthio group covalently bound to the active site cysteine ($^{112}$Cys). These results provide convincing evidence that the mechanism of action proposed in the scheme of FIGS. 1A-B is correct, and suggests that this may be the key pathway through which the N-alkylthio β-lactams operate.

The CoA disulfides (25a-c) were then tested for antibacterial activity against *S. aureus*. The alkyl methanethiolsulfonates (MTSs) (26a-c) used to produce the disulfides were also tested for anti-*Staphylococcus* activity. These tests (Table 2) show that, in every case, the CoA mixed disulfides were not active against *S. aureus*, but the corresponding MTSs were.

The efficacy of the MTSs supports the hypothesis that the intracellular production of mixed CoA disulfides is the source of biological activity. The apparent inactivity of the CoA mixed disulfides against bacteria does not detract from this hypothesis, since CoA analogs have been reported to have difficulty crossing the cell membrane (Clarke, K. M. et al. *J.*

Am. Chem. Soc., 2005, 237:11234-11235). These findings further suggest that the role of the N-alkylthio β-lactams may be to function as prodrugs to produce CoA mixed disulfides within the cytoplasm of susceptible bacteria.

TABLE 2

Zones of growth inhibition (mm) for CoA-alkyl disulfides 25a-c and alkyl methanethiolsulfonates 26a-c against a methicillin-susceptible strain of Staphylococcus aureus (S. aureus ATCC 25923) and 10 strains of methicillin-resistant S. aureus (MRSA): Zones given represent partial growth inhibition.

| Compound | S. aureus | MRSA |
|---|---|---|
| 25a | 0 | 0 |
| 25b | 0 | 0 |
| 25c | 0 | 0 |
| 26a | 22 | 23 |
| 26b | 19 | 20 |
| 26c | 23 | 23 |

In each case, 20 µg of the test compound in $CH_2Cl_2$ was applied to 6 mm cellulose disks prior to inoculation and incubation. The value corresponds to average diameter in mm (triplicate experiments) for the zone of growth inhibitions observed after 24 h of incubation at 37° C. S. aureus (ATCC 25923) and methicillin-resistant S. aureus (labeled MRSA USF652-659 and USF919-920) were obtained from Lakeland Regional Medical Center, Lakeland, Fla. Errors values are within ±1 mm.

In order to further explore the role of pathway (2), N-alkylthio β-lactams 2a and 2g were also tested against FabH. Surprisingly, both compounds exhibited inhibitory activity against purified E. coli FabH and M. tuberculosis FabH. Interestingly, the effect was much more pronounced for the FabH from E. coli (Table 3). It was also observed that the N-methylthio β-lactam was much more active than the sec-butylthio analog in both enzymes studied.

TABLE 3

Percent inhibition of FabH derived from E. coli (ecFabH) and M. tuberculosis (mtFabH) by N-alkylthio β-lactams 2a and 2g.[a]

| Compound | ecFabH[b] | mtFabH[c] |
|---|---|---|
| 2a | 89 | 75 |
| 2g | 30 | 4 |

[a]Measured as the percent decrease in activity of FabH in the presence of test compounds, as compared to the same enzyme in the absence of test compounds.
[b]Measured using 1 µM of test compound.
[c]Measured using 10 µM of test compound.

After measuring the inhibition of FabH by compounds 2a and 2g, the Reynolds group found that the activity of FabH was not regenerated by dialysis. However, activity of the FabH could be fully restored by treatment with dithiothreitol (DTT). This suggests that formation of the cysteine-alkyl disulfide is irreversible under buffered aqueous conditions, but that addition of a thiol, such as CoA or DTT, can reverse the effect through a thiol-disulfide exchange.

Despite this positive evidence, preliminary microbiological studies conducted by the Reynolds group have suggested that the FabH pathway may not be the primary pathway through which N-alkylthio β-lactams inhibit bacterial growth. Among their findings:

No significant formation of CoA mixed disulfides has been observed in cell extracts of Streptomyces coelicolor which have been treated with β-lactam.

The inhibitory effects of the β-lactams on FabH are greatly diminished when S. coelicolor extracts are used instead of merely buffer.

While these findings are noteworthy, it should be pointed out that S. coelicolor is reported to have mycothiol levels which are five times higher than the CoA levels.[10a]

If the thiol-transfer hypothesis is correct, this high thiol level will greatly reduce the efficacy of the N-alkylthio β-lactams against S. coelicolor, and thus these results may not correlate with what will ultimately be observed in Bacillus or Staphylococcus.

The activity of CoA mixed disulfides against purified FabH provides strong evidence that the N-alkylthio β-lactams function as prodrugs to produce mixed CoA disulfides within certain prokaryotic cells, and that these mixed disulfides inhibit the fatty acid cycle through inhibition of FabH. This mechanism is unique in that it involves a thiol-disulfide exchange from the mixed CoA disulfide to the active-site cysteine (FIGS. 1A-B). The capping may be considered to be semi-irreversible: because of the covalent nature of the cap, it cannot simply dissociate like a non-covalent inhibitor, but the cap can be removed and activity renewed through a thiol-disulfide exchange with an appropriate thiol. The mechanism proposed is supported by X-ray crystallographic studies.

Understanding the ability of CoA mixed disulfides to covalently deactivate bacterial fatty acid synthesis represents a major advance in the quest for novel antibacterials. Due to the demonstrated inability of CoA mixed disulfides to traverse the cell membrane, these CoA disulfides are not directly useful as therapeutics. However, in accordance with the present invention, these compounds can be produced in vivo through the use of any thiol transfer agent, including but not limited to, beta-lactams, alkyl methanethiolsulfonates (which are commercially available), or aryl alkyl disulfides (wherein the aryl contains a withdrawing group). For example, this research shows that prodrugs such as the N-alkylthio β-lactams can be used to produce the CoA mixed disulfides within the bacterial target.

Preliminary work done in the Reynolds laboratories has suggested that inhibition of FabH may not be the primary process by which the N-alkylthio β-lactams operate. However, if other mechanistic pathways exist, it is very possible that different CoA-dependent enzymes may also be inhibited. If this is the case, the profound new mode of action discovered in this study may be the first of many related strategies for the development of novel anti-infectives.

MATERIALS AND METHODS

General Chemical Methods.

Reagents were purchased from Sigma-Aldrich Chemical Company or Acros Chemical Company. Methanethiolsulfonates 26e and 26f were purchased from Toronto Research Chemicals. Reagents were used without further purification. Solvents were obtained from Fischer Scientific Company. Thin-layer chromatography (TLC) was carried out using EM Reagent plates with fluorescence indicator (SiO2-60, F-254). Products were purified by flash chromatography using J. T. Baker flash chromatography silica gel (40 µm). NMR spectra were recorded in $CDCl_3$ unless otherwise noted. $^{13}C$ NMR spectra were proton broad-band decoupled. Methylene chloride and THF were distilled prior to use. Prior to the preparation of disulfides, methanol was purged of oxygen by bubbling nitrogen an inert gas through it for several minutes.

m-Nitrobenzenethiol (43)

(Cashman, J. R. et al. Chem. Res. Toxicol., 1989, 2:392-399). To a solution of m-nitrobenzene disulfide (300 mg, 0.97 mmol) in anhydrous THF (2 mL) was added solid $NaBH_4$ (140 mg, 3.4 mmol) in small portions. The resulting mixture was stirred at room temperature under an inert atmosphere.

After 2 hr, the reaction mixture was cooled in an ice bath, and then about 5 mL of ice water was added to the mixture. The resulting mixture was acidified with HCl (1 M), then extracted with $CH_2Cl_2$ (10 mL). The organic layer was then washed with water (10 mL), then brine (10 mL), dried over $MgSO_4$, and concentrated in vacuo to give 43 (248 mg, 83%) as a pale yellow oil. $^1$H NMR ($CDCl_3$, 400 MHz): δ 8.10 (d, J=2.0 Hz, 1H); 7.97 (dd, J=8.0, 2.0 Hz, 1H); 7.54 (d, J=8.0 Hz, 1H); 7.38 (t, J=8.0 Hz, 1H); 3.68 (s, 1H); $^{13}$C NMR ($CDCl_3$, 100 MHz): δ 134.9, 130.0=, 123.9, 120.7.

o-Nitrobenzenethiol (44).

Prepared exactly as described for 43, except that the reaction was allowed to run for 3 h, and the products required chromatography (silica with hexanes:dichloromethane as eluent) to give 44 (160 mg, 61%) as a pale yellow flocculent solid. Mp: 44-45° C. $^1$H NMR ($CDCl_3$, 400 MHz): δ 8.24 (d, J=8.0 Hz, 1H); 7.42 (d, J=4.0 Hz, 1H); 7.29-7.24 (m, 1H); 4.00 (s, 1H). $^{13}$C NMR ($CDCl_3$, 100 MHz): δ 133.9, 132.2, 126.5, 126.0.

Synthesis of Aryl-Alkyl Disulfides: General Procedure.

To a 1.0 M solution of aryl thiol in MeOH (100 μl) was added a solution of alkyl methanethiolsulfonate (26a-f) in MeOH (105 μl of a 1.0 M solution, 1.05 eq.) After stirring at rt under an inert atmosphere for 1 h, the solutions were treated with a small amount (about 0.3 eq.) of cysteine hydrochloride in order to consume the excess MTS. The mixture was then concentrated under reduced pressure. The solid was taken up in DCM (1 mL), and the insoluble material was filtered off. The solution was stirred with Amberlyst-21 resin (weakly basic), (approx. 0.2 eq, preswelled in $CH_2Cl_2$) for 3 min. The solution was drawn off of the resin, quickly passed through a small silica plug using dichloromethane, and concentrated in vacuo to give the desired product.

3,4-Difluorophenyl Methyl Disulfide (33a).

Isolated 9.6 mg (50%) as a colorless oil. $^1$H NMR (250 MHz, $CDCl_3$): δ 7.37-7.29 (m, 1H); 7.18-7.00 (m, 2H); 2.34 (s, 3H).

3,4-Difluorophenyl Ethyl Disulfide (33b).

Isolated 8.5 mg (42%) as a colorless oil. $^1$H NMR (250 MHz, $CDCl_3$): δ 7.37-7.29 (m, 1H); 7.18-7.00 (m, 2H); 2.69 (q, J=7.4 Hz, 2H); 1.24 (t, J=7.4 Hz, 3H).

3,4-Difluorophenyl Isopropyl Disulfide (33c).

Isolated 11.5 mg (53%) as a colorless oil. $^1$H NMR (250 MHz, $CDCl_3$): δ 7.37-7.29 (m, 1H); 7.18-712 (m, 1H); 7.08-6.96 (m, 1H); 2.99 (septet, J=6.8 Hz, 1H); 1.22 (d, J=6.8 Hz, 6H).

Sec-Butyl 3,4-Difluorophenyl Disulfide (33d).

Isolated 15 mg (65%) as a colorless oil. $^1$H NMR (250 MHz, $CDCl_3$) δ 7.37-7.29 (m, 1H); 7.19-7.12 (m, 1H); 7.07-6.97 (m, 1H); 2.80-2.38 (m, 1H); δ 1.68-1.54 (m, 1H); 1.54-1.39 (m, 1H); 1.20 (d, J=6.8 Hz, 3H); 0.88 (t, J=7.4 Hz, 3H).

3,4-Difluorophenyl n-propyl Disulfide (33e).

Isolated 11.8 mg (54%) as a colorless oil. $^1$H NMR (400 MHz, $CDCl_3$): δ 7.40-7.35 (m, 1H); 7.21-7.19 (m, 1H); 7.09 (q, J=8.8 Hz, 1H); 2.69 (t, J=7.0 Hz, 2H); 1.66 (tt, J=7.2, 7.0 Hz, 2H); 0.95 (t, J=7.2 Hz, 3H).

n-Butyl 3,4-difluorophenyl Disulfide (33f).

Isolated 4.9 mg (43%) as a colorless oil. $^1$H NMR (400 MHz, $CDCl_3$): δ 7.40-7.35 (m, 1H); 7.21-7.19 (m, 1H); 7.09 (q, J=8.8 Hz, 1H); 2.71, (t, J=6.8 Hz, 2H); 1.61 (tt, J=7.2, 7.2 Hz, 2H); 1.37 (tq, J=7.4, 7.2 Hz, 2H); 0.87 (t, J=7.4 Hz, 3H).

o-Chlorophenyl Ethyl Disulfide (34b).

Isolated 12.0 mg (59%) as a colorless oil. $^1$H NMR (250 MHz, $CDCl_3$): δ 7.73 (dd, J=7.9, 1.5 Hz, 1H); 7.28-7.19 (m, 2H); 7.07 (dt, J=1.6, 7.6 Hz, 1H); 2.68 (q, J=7.3 Hz, 2H); 1.25 (t, J=7.3 Hz, 3H).

o-Chlorophenyl Isopropyl Disulfide (34c).

Isolated 17.3 mg (80%) as a colorless oil. $^1$H NMR (250 MHz, $CDCl_3$): δ 7.84 (dd, J=8.0, 1.6 Hz, 1H); 7.37-7.28 (m, 2H); 7.16 (dt, J=1.6, 7.6 Hz, 1H); 3.10 (septet, J=6.8 Hz, 1H); 1.35 (d, J=6.8 Hz, 6H).

s-Butyl o-chlorophenyl Disulfide (34d).

Isolated 29.6 mg (100%) as a colorless oil. $^1$H NMR (250 MHz, $CDCl_3$): δ 7.74 (dd, J=7.9, 1.5 Hz, 1H); 7.26-7.17 (m, 2H); 7.05 (dt, J=1.6, 7.6 Hz, 1H); 2.81-2.69 (m, 1H); 1.72-1.57 (m, 1H); 1.56-1.42 (m, 1H); 1.22 (d, J=6.8 Hz, 3H); 0.90 (t, J=7.4 Hz, 3H).

o-Chlorophenyl n-propyl Disulfide (34e).

Isolated 8 mg (37%) as a colorless oil. $^1$H NMR (400 MHz, $CDCl_3$): δ 7.79 (dd, J=8.0, 1.2 Hz, 1H); 7.32-7.14 (m, 2H); 7.0 (t, J=7.0 Hz, 1H); 2.69 (t, J=7.4 Hz, 2H); 1.67 (tq, J=7.4, 7.2 Hz, 2H); 0.967 (t, J=7.2 Hz, 3H).

n-Butyl o-chlorophenyl Disulfide (34f).

Isolated 17.5 mg (76%) as a colorless oil. $^1$H NMR (400 MHz, $CDCl_3$): δ 7.78 (d, J=8.0 Hz, 1H); 7.32-7.24 (m, 2H); 7.12 (t, J=7.8 Hz, 1H); 2.71 (t, J=7.2 Hz, 2H); 1.66-1.61 (m, 2H); 1.46-1.42 (m, 2H); 0.90 (t, J=7.8 Hz, 3H).

3,4-Dimethylphenyl Methyl Disulfide (35a).

Isolated 9.7 mg (53%) as a colorless oil. $^1$H NMR (250 MHz, $CDCl_3$): δ 7.22 (d, J=8.4 Hz, 1H); 7.18 (s, 1H); 7.02 (d, J=7.7 Hz, 1H); 0.37 (s, 3H); 2.19 (s, 3H); 2.18 (s, 3H).

3,4-Dimethylphenyl ethyl disulfide (35b). Isolated 13.0 mg (66%) as a colorless oil. $^1$H NMR (250 MHz, $CDCl_3$): δ 7.24-7.17 (m, 2H); 7.0 (d, J=7.5 Hz, 1H); 2.67 (q, J=6.9 Hz, 2H); 2.184 (s, 3H); 2.166 (s, 3H); 1.24 (t, J=7.4 Hz, 3H).

3,4-Dimethylphenyl Isopropyl Disulfide (35c).

Isolated 4.0 mg (19%) as a colorless oil. $^1$H NMR (250 MHz, $CDCl_3$): 7.23-7.19 (m, 2H); 7.00 (d, J=7.8 Hz, 1H); 2.99 (septet, J=6.8 Hz, 1H); 2.18 (s, 3H); 2.16 (s, 3H); 1.23 (d, J=6. Hz, 6H).

sec-Butyl 3,4-dimethylphenyl Disulfide (35d).

Isolated 8.5 mg (38%) as a colorless oil. $^1$H NMR (250 MHz, $CDCl_3$): δ 7.23-7.15 (m, 2H); 7.00 (d, J=7.6 Hz, 1H); 2.79-2.68 (m, 1H); 2.18 (s, 3H); 2.16 (s, 3H); 1.70-1.56 (m, 1H); 1.53-1.36 (m, 1H); 1.21 (d, J=6.8 Hz, 3H); 0.87 (t, J=7.4 Hz, 3H).

3,4-Dimethylphenyl n-propyl Disulfide (35e).

Isolated 10.0 mg (48%) as a colorless oil. $^1$H NMR (400 MHz, $CDCl_3$): δ 7.28-7.24 (m, 2H); 7.06 (d, J=7.2 Hz, 1H); 2.67 (t, J=7.0 Hz, 2H); 2.24 (s, 3H); 2.22 (s, 3H); 1.72 (tq, J=7.0, 7.4 Hz, 2H); 0.95 (t, J=7.4 Hz, 3H).

n-Butyl 3,4-dimethylphenyl Disulfide (35f).

Isolated 17.8 mg (79%) as a colorless oil. $^1$H NMR shows about 20% of material is unreacted 26f. $^1$H NMR (400 MHz, $CDCl_3$): δ 7.28-7.24 (m, 2H); 7.06 (d, J=7.2 Hz, 1H); 2.71 (t, J=7.4 Hz, 2H); 2.24 (s, 3H); 2.22 (s, 3H); 1.62 (m, 2H); 1.37 (m, 2H); 0.87 (t, J=7.2 Hz, 3H).

m-Ethoxyphenyl Methyl Disulfide (36a).

Isolated 5.6 mg (28%) as a colorless oil. $^1$H NMR (400 MHz, $CDCl_3$): δ 7.21 (t, J=8.0 Hz, 1H); 7.09-7.05 (m, 2H); 6.74 (dd, J=8.0, 1.2 Hz, 1H); 4.04 (q, J=7.1 Hz, 2H); 2.43 (s, 3H); 1.41 (t, J=7.4 Hz, 3H).

p-Nitrophenyl Methyl Disulfide (38a).

Isolated 15.3 mg (76%) as a yellow oil. $^1$H NMR (400 MHz, $CDCl_3$): δ 8.17 (d, J=8.8 Hz, 2H); 7.63 (d, J=8.8 Hz, 2H); 2.46 (s, 3H). Resynthesis using 10× scale yielded 184 mg (92%) as a slightly oily, bright yellow solid. Mp: 29-32° C. $^{13}$C NMR (100 MHz, $CDCl_3$): δ 126.6, 126.0, 124.7, 124.4, 22.9.

Ethyl p-nitrophenyl Disulfide (38b).

$^1$H NMR (400 MHz, $CDCl_3$): δ 8.14 (d, J=8.8 Hz, 2H); 7.64 (d, J=8.8 Hz, 2H); 2.77 (q, J=7.0 Hz, 2H); 1.31 (t, J=7.2 Hz, 3H).

Isopropyl p-nitrophenyl disulfide (38c). $^1$H NMR (400 MHz, CDCl$_3$): δ 8.14 (d, J=8.8 Hz, 2H); 7.64 (d, J=8.8 Hz, 2H); 3.10 (septuplet, J=6.5 Hz, 1H); 1.30 (d, J=6.8 Hz, 6H).

Sec-Butyl p-nitrophenyl Disulfide (38d).

$^1$H NMR (400 MHz, CDCl$_3$): δ 8.14 (d, J=8.8 Hz, 2H); 7.64 (d, J=8.8 Hz, 2H); 2.88-2.83 (m, 1H); 1.73-1.64 (m, 1H); 1.57-1.50 (m, 1H); 1.27 (d, J=6.8 Hz, 3H); 0.97 (t, J=7.2 Hz, 3H).

p-Nitrophenyl n-propyl Disulfide (38e).

$^1$H NMR (400 MHz, CDCl$_3$): δ 8.14 (d, J=8.8 Hz, 2H); 7.63 (d, J=8.8 Hz, 2H); 2.73 (t, J=7.2 Hz, 2H); 1.68 (tq, J=7.2, 7.6 Hz, 2H); 0.98 (t, J=7.6 Hz, 3H).

n-Butyl p-nitrophenyl Disulfide (38f).

$^1$H NMR (400 MHz, CDCl$_3$): δ 8.15 (d, J=8.0 Hz, 2H); δ 7.64 (d, J=8.8 Hz, 2H); δ 2.95 (t, J=7.4 Hz, 2H); δ 1.65-1.61 (m, 2H); δ 1.42-1.37 (m, 2H); δ 0.88 (t, J=7.2 Hz, 3H).

p-Aminophenyl Methyl Disulfide (39a).

To a solution of p-aminobenzenethiol (125 mg, 1 mmol) in methanol (1 ml) was added MMTS (94 µl, 1 mmol) in a single portion. The reaction was stirred at RT under N$_2$. After 2 hr, the solution was loaded onto an SCX column and eluted with methanol, followed by 1M ammonia in methanol. The basic eluents were concentrated in vacuo to a yellow oil. Chromatography (1:1 hexanes:CH$_2$Cl$_2$ with 1% isopropylamine) yielded 39a (140 mg, 82%) as a pale yellow oil. $^1$H NMR (250 MHz, CDCl$_3$): δ 7.28 (d, J=8.6 Hz, 2H); 6.54 (d, J=8.6 Hz, 2H); 3.60 (broad s, 2H); 2.34 (s, 3H). Treatment with HCl/ether gave 5 mg of the HCl salt. Biological testing was performed on the acid salt. $^1$H NMR (400 MHz, d$_6$-DMSO): δ 7.46 (broad s, 2H); 7.05 (broad s, 2H); 2.47 (s, 3H); 2.43 (s, 3H).

p-Acetamidophenyl Methyl Disulfide (46a).

To a solution of 39a (50 mg, 0.3 mmol) in dry CH$_2$Cl$_2$ (3 ml) was added triethylamine (127 µL, 0.9 mmol, 3 eq.), followed by acetyl chloride (32 µL, 0.45 mmol). The reaction was stirred at RT for 1 hr., then was diluted with dichloromethane, washed with water, then 5% aq. HCl, then 5% aq. NaHCO$_3$. Dried over MgSO$_4$, then concentrated in vacuo to give a yellow oil which solidified on standing. Chromotography (1:1 petroleum ether:ethyl acetate) gave 18 mg (29%) as a light brown solid. $^1$H NMR (400 MHz, CDCl$_3$): δ 7.47 (s, 4H); 2.41 (s, 3H); 2.16 (s, 3H).

o-(Hydroxymethyl)phenyl Methyl Disulfide (41a).

$^1$H NMR (400 MHz, CDCl$_3$): δ 7.73 (d, J=8.8 Hz, 1H); 7.44 (dd, J=6.6, 2.2 Hz, 1H); 7.32-7.24 (m, 2H); 4.83 (d, J=5.2 Hz, 2H); 2.42 (s, 3H); 2.02 (broad t, J=6.0 Hz, 1H).

Methyl 2-pyridinyl Disulfide (42a).

Indicates about 10% of material is unreacted 26a. $^1$H NMR (400 MHz, CDCl$_3$): δ 8.46 (d, J=4.4 Hz, 1H); 7.68-7.61 (m, 2H); 7.07 (t, J=6.6 Hz, 1H); 2.49 (s, 3H).

Ethyl 2-pyridinyl Disulfide (42b).

After the general procedure, NMR indicated the presence of unreacted methanthiolsulfonate, so the compound was further purified by silica chromatography (5% ethyl acetate in hexanes as eluent) to give pure 42b (2.3 mg, 13%) as a colorless liquid. $^1$H NMR (400 MHz, CDCl$_3$): δ 8.43 (d, J=4.4 Hz, 1H); 7.71 (d, J=8.0 Hz, 1H); 7.61 (t, J=7.0 Hz, 1H); 7.05 (dd, J=5.2, 7.2 Hz, 1H); 2.79 (q, J=7.3 Hz, 2H); 1.31 (t, J=7.3 Hz, 3H).

Isopropyl 2-pyridinyl Disulfide (42c).

After the general procedure, NMR indicated the presence of unreacted methanthiolsulfonate, so the compound was further purified by silica chromatography (5% ethyl acetate in hexanes as eluent) to give pure 42c (5.6 mg, 30%) as a colorless liquid. $^1$H NMR (400 MHz, CDCl$_3$): 8.42 (d, J=3.6 Hz, 1H); 7.73 (d, J=8.0 Hz, 1H); 7.60 (dt, J=7.8, 1.8 Hz, 1H); 7.03 (dd, J=4.8, 6.8 Hz, 1H); 3.11 (septet, J=6.8 Hz, 1H); 1.30 (d, J=6.8 Hz, 6H).

s-Butyl 2-pyridinyl Disulfide (42d).

After the general procedure, NMR indicated the presence of unreacted methanthiolsulfonate, so the compound was further purified by silica chromatography (5% ethyl acetate in hexanes as eluent) to give pure 42d (3.9 mg, 20%) as a colorless liquid. $^1$H NMR (400 MHz, CDCl$_3$): δ 8.43 (d, J=4.4 Hz, 1H); 7.75 (d, J=7.8 Hz, 1H); 7.62 (t, J=7.6 Hz, 1H); 7.05 (t, J=5.8 Hz, 1H); 2.91-2.86 (m, 1H); 1.77-1.69 (m, 1H); 1.60-1.49 (m, 1H); 1.30 (d, J=6.8 Hz, 3H); 0.98 (t, J=7.2 Hz, 3H).

Methyl m-nitrophenyl Disulfide (43a).

Isolated 7.6 mg (38%) as a colorless oil. $^1$H NMR (400 MHz, CDCl$_3$): δ 8.39 (s, 1H); 8.04 (d, J=6.4 Hz, 1H); 7.79 (d, J=8.0 Hz, 1H); 7.49 (t, J=8.0 Hz, 1H); 2.47 (s, 3H).

Ethyl m-nitrophenyl Disulfide (43b).

Isolated 7.7 mg (36%) as a colorless oil. $^1$H NMR (400 MHz, CDCl$_3$): δ 8.41 (s, 1H); 8.02 (d, J=7.2 Hz, 1H); 7.80 (d, J=7.2 Hz, 1H); 7.47 (t, J=7.2 Hz, 1H); 2.78 (q, J=7.3 Hz, 2H); 1.32 (t, J=7.2 Hz, 3H).

Isopropyl m-nitrophenyl Disulfide (43c).

Isolated 17.0 mg (75%) as a colorless oil. $^1$H NMR (400 MHz, CDCl$_3$): δ 8.41 (s, 1H); 8.01 (d, J=8.0 Hz, 1H); 7.80 (d, J=7.2 Hz, 1H); 7.46 (t, J=7.2 Hz, 1H); 3.09 (septet, J=6.8 Hz, 1H); 1.30 (d, J=6.8 Hz, 6H).

s-Butyl m-nitrophenyl Disulfide (43d).

Isolated 12.6 mg (52%) as a colorless oil. $^1$H NMR (400 MHz, CDCl$_3$): δ 8.42 (s, 1H) 8.00 (d, J=8.0 Hz, 1H); 7.80 (d, J=8.0 Hz, 1H); 7.45 (t, J=8.0 Hz, 1H); 2.88-2.83 (m, 1H); 1.73-1.68 (m, 1H); 1.57-1.50 (m, 1H); 1.28 (d, J=7.2 Hz, 3H); 0.97 (t, J=7.2 Hz, 3H).

Methyl o-nitrophenyl Methyl Disulfide (44a).

Isolated 13.9 mg (69%) as an oily yellow solid. $^1$H NMR (400 MHz, CDCl$_3$): δ 8.27-8.23 (m, 2H); 7.69 (t, J=7.4 Hz, 1H); 7.35 (d, J=7.2 Hz, 1H); 2.41 (s, 3H).

Ethyl o-nitrophenyl Ethyl Disulfide (44b).

Isolated 13.2 mg (62%) as an oily yellow solid. $^1$H NMR (400 MHz, CDCl$_3$): δ 8.28 (d, J=8.0 Hz, 1H); 8.24 (d, J=8.0 Hz, 1H); 7.66 (t, J=7.4 Hz, 1H); 7.33 (t, J=7.6 Hz, 1H); 2.74 (q, J=7.3 Hz, 2H); 1.31 (t, J=7.2 Hz, 3H).

Isopropyl o-nitrophenyl Disulfide (44c).

Chromatographed on silica with 3% dichloromethane in hexanes as eluent. Isolated 13.7 mg (60%) as a yellow oil. $^1$H NMR (400 MHz, CDCl$_3$): δ 8.28 (d, J=8.8 Hz, 1H); 8.23 (d, J=8.8 Hz, 1H); 7.64 (t, J=7.9 Hz, 1H); 7.31 (t, J=7.6 Hz, 1H); 3.05 (s, J=6.8 Hz, 1H); 1.31 (d, J=6.8 Hz, 6H).

s-Butyl o-nitrophenyl Disulfide (44d).

Chromatographed on silica with 3% dichloromethane in hexanes as eluent. Isolated 12.9 mg (54%) as a yellow oil. $^1$H NMR (400 MHz, CDCl$_3$): δ 8.29 (d, J=8.0 Hz, 1H); 8.22 (d, J=8.8 Hz, 1H); 7.64 (t, J=7.8 Hz, 1H); 7.31 (t, J=8.0 Hz, 1H); 2.86-2.79 (m, 1H); 1.75-1.60 (m, 1H); 1.58-1.50 (m, 1H); 1.28 (d, J=7.2 Hz, 3H); 0.98 (t, J=7.8 Hz, 3H).

General Biological Methods.

*Staphylococcus aureus* (ATCC 25923) and MRSA (ATCC 43300 and 33591) were purchased from ATCC sources. Eight additional strains of MRSA were obtained from Lakeland Regional Medical Center (Lakeland, Fla.). *Bacillus* bacteria (USF 848) from Sterne spore vaccine was purchased from Colorado Serum Co., Denver, Colo.

Culture Preparation.

From a freezer stock in tryptic soy broth (Difco Laboratories, Detroit, Mich.) and 20% glycerol, a culture of each microorganism was transferred with a sterile Dacron swab to TRYPTICASE Soy Agar (TSA) plates (Becton-Dickinson Laboratories, Cockeysville, Md.), streaked for isolation, and incubated at 37° C. for 24 h. A $10^8$ standardized cell count suspension was then made in sterile phosphate-buffered saline (pH 7.2) and swabbed across fresh TSA plates.

Antimicrobial Testing: Kirby-Bauer Method.

Sterile saline (5 mL) was inoculated with a swab of bacteria, and then the concentration was adjusted to 0.5 McFarland standard. Bacterial solution was then streaked across a TSA plate to give an even lawn of bacteria. 1-µL sterile pipet tips were used to drill 6 mm wells into the agar plate, then 20 µL of 1 mg/mL drug in DMSO was added to the well. Plates were inoculated overnight at 37° C.

Agar Dilution Minimal Inhibitory Concentration (MIC) Assay.

The antimicrobial and nanoparticle emulsion concentrations analyzed were determined by the standard NCCLS protocol M7-A2 (National Committee for Clinical Laboratory Standards, Methods for Dilution of Antimicrobial Susceptibility Tests for Bacteria that Grow Aerobically; NCCLS Document M7-A4, 1997, Vol. 17(2)), and these concentrations were pipeted into a pre-determined well of a 24 well plate. Muller Hinton agar was added to each well in liquid form to produce total well volumes of 1.5 mL. The contents of each well were thoroughly stirred to evenly distribute the antimicrobial solution within the agar. Once the agar solidified, 10 µL of sterile saline containing 0.5 McFarland Standard of the desired bacteria was pipeted on top of each agar and the plates were then incubated for 24 hours at 37° C. Bacterial growth was assessed by visual observation of growth.

Measurement of $^3$H Acetate Uptake.

The following experiments were carried out by Dr. Seyoung Jang. A culture of *S. aureus* (strain RN4220 in 1% Luria Broth) was used as 1% inoculum into fresh medium (20 mL) and cells were grown at 37° C. until the $A_{600}$ reached 0.11 ($1.3 \times 10^7$ cfu/mL). To a sample of culture was then added sufficient drug in DMSO such that the final concentration of DMSO in each sample was 2% by volume, and each sample contained one of the following: a.) Penicillin G, (2 ug/mL, 2×MIC); b.) Lactam 8 (10 µg/mL, 1×MIC); c.) Lactam 8 (20 µg/mL, 2×MIC); d.) no drug added.

Each tube was incubated 5 min. at 37° C., and then 2 µl of $^3$H-acetate (10 µCi/uL in ethanol solution, sodium salt) were added to each tube (4 µCi/mL radioactivity per tube). At intervals of 15, 30, 45, and 60 min, 0.8 mL aliquots were taken from each tube, homogenized, and diluted with chloroform (1 mL) and methanol (2 mL). An additional 1 mL of chloroform was added, and the solution mixed. The organic solution was then washed with distilled water (1 mL), then 2M aq. KCl (3×1 mL), then 0.1 M aq. sodium acetate (3×1 mL). The radioactivity in the organic phase was then analyzed by scintillation counting.

Enzyme Expression and Purification.

The ecFabH and sgFabD protein was overexpressed in *E. coli* with N-terminal polyhistidine tag and subsequently purified by metal chelation chromatography as described previously (He, X. and Reynolds, K. A. *Antimicrob. Agents Chemother.*, 2002, 46(5):1310-1318; He, X. et al. *Anal. Biochem.*, 2000, 282:107-114).

FabH Enzyme Assay.

FabH assays were carried out using a standard coupled trichloroacetic acid precipitation assay which determines the rate of formation of radiolabeled 3-ketoacyl ACP from malonyl ACP and radiolabeled acetyl CoA. In this coupled assay *Streptomyces glauscescens* FabD is used to generate the malonyl ACP substrate from malonyl CoA and *Streptomyces glauscescens* ACP (Lobo, S. et al. *Biochemistry*, 2001, 40:11955-11964). For inhibition studies, the test compounds were incubated with ecFabH for 15 min at room temperature (23° C.) prior to addition to a solution of [1-$^{17}$C]acetyl-CoA and MACP. The $IC_{50}$ (concentration of inhibitor at which 50% inhibition of ecFabH is achieved) was determined by duplicate assays with a minimum of six concentrations of inhibitor. The $IC_{50}$ values were calculated with Grafit 4.012 (Middlesex, United Kingdom).

EXAMPLE 1

Synthesis of Aryl-Alkyl Disulfides

In order to quickly synthesize a large number of aryl alkyl disulfides for screening, it was desirable to develop a preparation that was simple, easy to perform repeatedly, and which required minimal purification of the product disulfides. After testing a variety of conditions, it was found that this could be accomplished by combining a methanolic solution of thiol (100 µL of 1.0 M) with a slight excess of the alkyl methanethiolsulfonate (MTS) (105 µL of 1.0 M methanolic solution). After stirring under an inert atmosphere for 1 hr, the solutions were treated with a small amount (about 0.3 eq.) of cysteine hydrochloride, in order to consume the excess MTS. The solution was then concentrated in vacuo, taken up in dichloromethane (1 mL), filtered to remove any cysteine products, treated with Amberlyst-21 resin (weakly basic), then flushed through a small silica plug to remove impurities. In most instances, this yielded products >90% pure by $^1$H NMR.

Following this general procedure (FIG. 10), disulfides were prepared by combining an array of thiols with various thiolating agents (FIGS. 11A-J). Yields for the initial set of reactions are shown in Table 4.

TABLE 4

Yields from the semi-combinatorial synthesis of aryl-alkyl disulfides.

| | 33 | 34 | 35 | 36 | 37 | 38 | 39 | 40 | 41 | 42 |
|---|----|----|----|----|----|----|----|----|----|----|
| a | 50 | —[a] | 53 | 28 | 0 | 76 | 82 | 0 | 44 | 35 |
| b | 42 | 59 | 66 | —[a] | — | 48 | — | — | — | 25 |
| c | 53 | 80 | 19 | — | — | 70 | — | — | — | 10 |
| d | 65 | 100 | 38 | — | — | 63 | — | — | — | 15 |
| e | 54 | 37 | 48 | — | — | 81 | — | — | — | — |
| f | 43 | 76 | 79 | — | — | 63 | — | — | — | — |

[a]"—" indicates a reaction was not run.

EXAMPLE 2

Activity Against Methicillin-Susceptible *Staphylococcus aureus*

Antibacterial assays of disulfides 33-45 were performed on methicillin-susceptible *Staphylococcus aureus* (MSSA; ATCC 25923) by Kirby-Bauer well diffusion on agar plates according to NCCLS guidelines (National Committee for Clinical Laboratory Standards, Methods for Dilution of Antimicrobial Susceptibility Tests for Bacteria that Grow Aerobically; NCCLS Document M7-A4, 1997, Vol. 17(2)). The zones of growth inhibition produced by the compounds against this microbe after 24 h of incubation at 37° C. are presented in Table 5. These results show that while the more lipophilic (33-35) disulfides are inactive, the p-nitrophenyl disulfides (38a-f) show extraordinary activity. Within the 2-pyridinyl disulfide series (42), the methyl (42a) and ethyl (42b) disulfides showed some activity.

TABLE 5

Zones of growth inhibition (mm) of S. aureus
(ATCC 25923) for aryl-alkyl disulfides.

|   | 33 | 34 | 35 | 36 | 38 | 39 | 41 | 42 | 43 | 44 | 46 |
|---|---|---|---|---|---|---|---|---|---|---|---|
| a | (11)[a] | — | (10) | (9) | 30(35) | 0 | (14) | 16(23) | 27(36) | 34(37) | (20) |
| b | (9) | (9) | 0 | — | 47(54) | — | — | (21) | (45) | 29(40) | — |
| c | (9) | (11) | (9) | — | 68(85) | — | — | 0 | 55(85) | 17(31) | — |
| d | (9) | (10) | 0 | — | 47(68) | — | — | 0 | 25(45) | 15(24) | — |
| e | 0 | 0 | 0 | — | 36(43) | — | — | — | — | — | — |
| f | (10) | (9) | 0 | — | 41(53) | — | — | — | — | — | — |

In each case, 20 µg of the test compound in DMSO was applied to 6 mm cellulose disks prior to inoculation and incubation. The value corresponds to average diameter in mm (duplicate experiments) for the zone of growth inhibitions observed after 24 h of incubation at 37° C. Errors values are within ±1 mm. [a.] numbers in parentheses represent areas of partial inhibition.

EXAMPLE 3

Synthesis of Second-Round Disulfides and Activity Against Methicillin-Susceptible S. aureus and Methicillin-Resistant S. aureus Based on the profound efficacy of disulfide set 38a-f, it seemed worthwhile to focus attention on the preparation of compounds which (a) contained the nitro group in other positions on the aryl ring, or (b) contained aryl substituents which mimicked the electron-withdrawing and/or hydrogen bond accepting nature of the para-nitrophenyl compounds. To this end, the meta-nitrophenyl disulfides (43a-f) and ortho-nitrophenyl disulfides (44a-f) were prepared by the general procedure described above (FIG. 14A). Additionally, disulfide 46a was prepared by the acetylation of 39a (FIG. 14B). The Kirby-Bauer data for these compounds are shown in Table 6.

TABLE 6

Zones of growth inhibition (mm) of S. aureus (ATCC 25923)
for aryl-alkyl disulfides.

|   | 43 | 44 | 46 |
|---|---|---|---|
| a | 27 (36) | 34 (37) | (20) |
| b | (45) | 29 (40) | — |
| c | 55 (85) | 17 (31) | — |
| d | 25 (45) | 15 (24) | — |

In each case, 20 µg of the test compound in DMSO was applied to 6 mm cellulose disks prior to inoculation and incubation. The value corresponds to average diameter in mm (duplicate experiments) for the zone of growth inhibitions observed after 24 h of incubation at 37° C. Errors values are within ±1 mm. [a.] numbers in parentheses represent areas of partial inhibition.

For compounds which showed activity in the Kirby-Bauer assays, the minimum inhibitory concentrations (MIC) against methicillin-susceptible S. aureus (MSSA) were also determined, as shown in Table 7. The compounds were further tested by Kirby-Bauer assay against methicillin-resistant S. aureus (MRSA). These results are shown in Table 8.

TABLE 7

Minimum inhibitory concentration (MIC)[a] (µg/mL) of
active compounds against S. aureus (ATCC 25923).

|   | 38 | 41 | 42 | 43 | 44 |
|---|---|---|---|---|---|
| a | 16 | 64 | 64 | 16 | 64 |
| b | 32 | — | 32 | 48 | 16 |
| c | 0.4 | — | — | 0.4 | 6 |
| d | 0.8 | — | — | 2 | 16 |
| e | 24 | — | — | — | — |
| f | 32 | — | — | — | — |

[a]This indicates the lowest concentration of drug (in µg/mL) where bacterial growth is visibly inhibited. Values were determined by serial dilution in a 24-well plate according to NCCLS protocols (National Committee for Clinical Laboratory Standards, Methods for Dilution of Antimicrobial Susceptibility Tests for Bacteria that Grow Aerobically; NCCLS Document M7-A4, 1997, Vol. 17(2)).

TABLE 8

Average zones of growth inhibition (mm) of MRSA
(USF-652-659, 919-920) for aryl-alkyl disulfides.

|   | 38 | 43 | 44 |
|---|---|---|---|
| a | 23 | 15 | 26 |
| b | 38 | 12 | —[a] |
| c | 75[b] | 38 | 20 |
| d | 54 | 22 | — |
| e | 38 | — | — |
| f | 28 | — | — |

In each case, 20 µg of the test compound in DMSO was applied to 6 mm cellulose disks prior to inoculation and incubation. The value corresponds to average diameter in mm observed after 24 h of incubation at 37° C. (duplicate experiments) for 10 strains of methicillin-resistant S. aureus (MRSA, labeled USF652-659 and USF919-920. [a.] "--" not run. [b.] This value represents the average from USF659, USF919. Currently being retested on other strains This value represents the average from USF 652-654, 659. Currently being retested on other strains.

Compounds in the nitrophenyl disulfide series are, by far, the most potent antibacterial agents prepared to date in this laboratory, especially the meta and para series. The zones of inhibition of the isopropyl and sec-butyl compounds are substantially larger than the zones of the best N-alkylthio β-lactams developed previously in the Turos laboratories. Further, the zones of inhibition are considerably larger than many commercial antibiotics, including penicillin G and Ciprofloxacin (Table 9).

TABLE 9

Figure 7A:
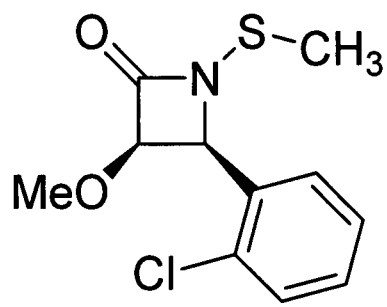
FIGS. 7A-B show compounds 2a and 2g, respectively.
Figure 7B:
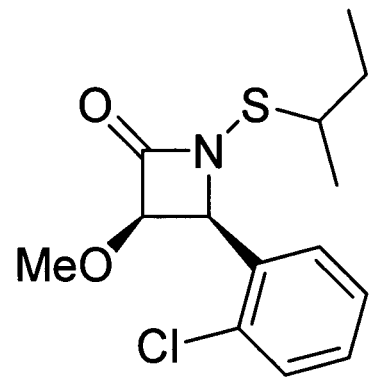
Figure 9:
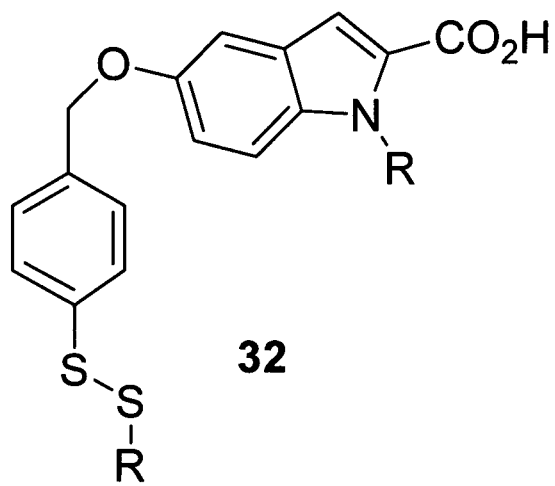
FIG. 9 shows the structure of compound 32, wherein R=methyl, ethyl, s-butyl, n-butyl, n-octyl, or n-decyl.
Figure 12:
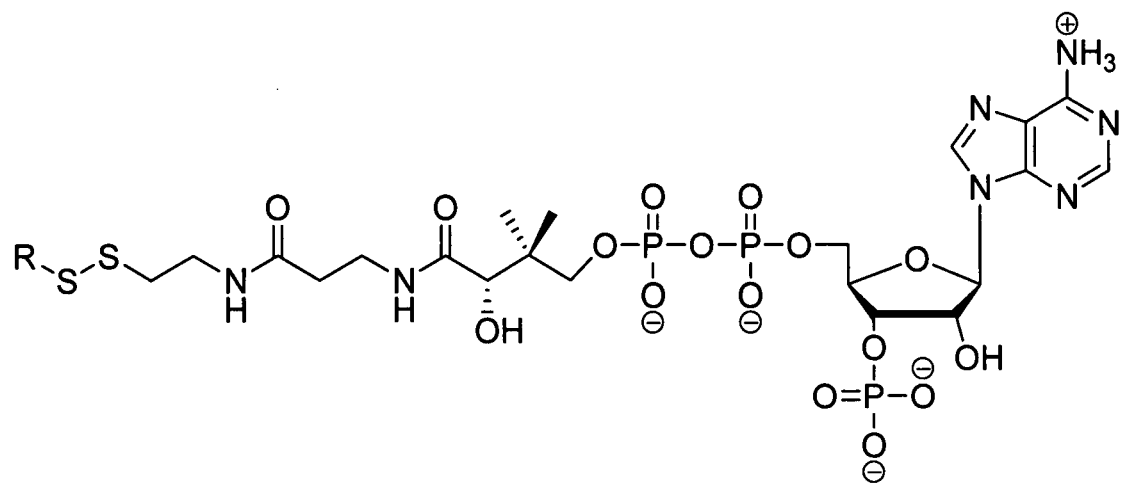
FIG. 12 shows the chemical structure of mixed CoA disulfides (25a-f), wherein: for 25a, R=methyl; for 25b, R=ethyl; 25c, R=s-butyl; for 25d, R=n-butyl; for 25e, R=n-octyl; and for 25f, R=n-decyl.
Figure 13:
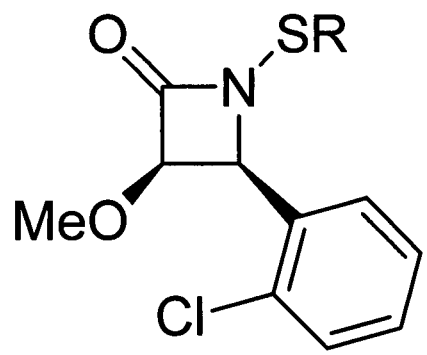
FIG. 13 shows the structures of compounds 2a and 2g, wherein R=methyl and s-butyl, respectively.
Figure 17:
FIG. 17 shows the chemical structure of compound 12.
Figure 18:
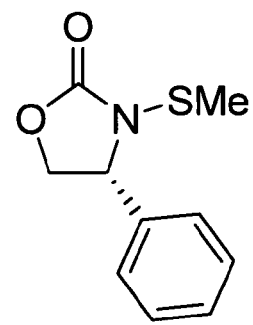
FIG. 18 shows the chemical structure of compound 13.
Figure 19:
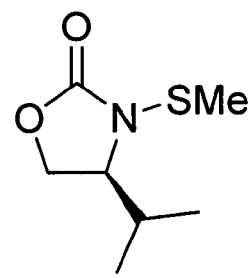
FIG. 19 shows the chemical structure of compound 14.
Figure 20:
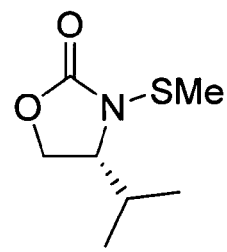
FIG. 20 shows the chemical structure of compound 15.
Figure 21:
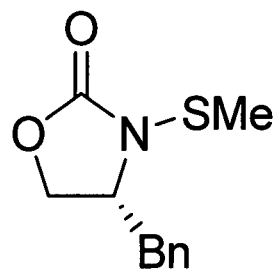
FIG. 21 shows the chemical structure of compound 16.
Figure 22:
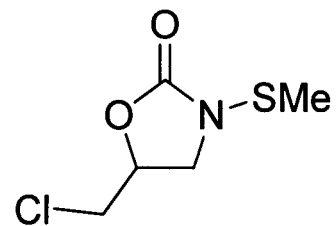
FIG. 22 shows the chemical structure of compound 17.
Figure 23:
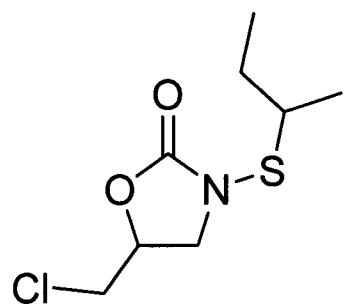
FIG. 23 shows the chemical structure of compound 18.
Figure 24:
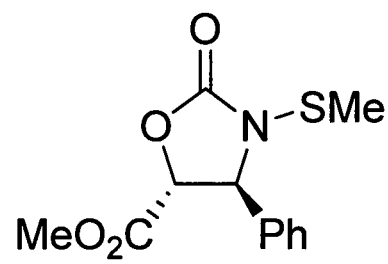
FIG. 24 shows the chemical structure of compound 19.
Figure 25:
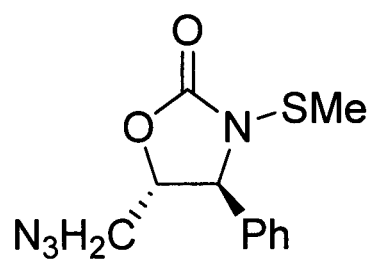
FIG. 25 shows the chemical structure of compound 20.
Figure 26:
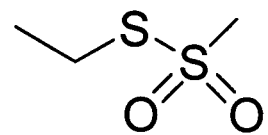
FIG. 26 shows the chemical structure of compound 26b.
Figure 27:
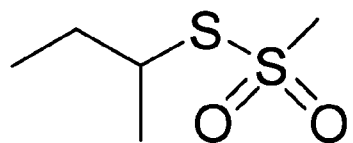
FIG. 27 shows the chemical structure of compound 26c.
Figure 28:
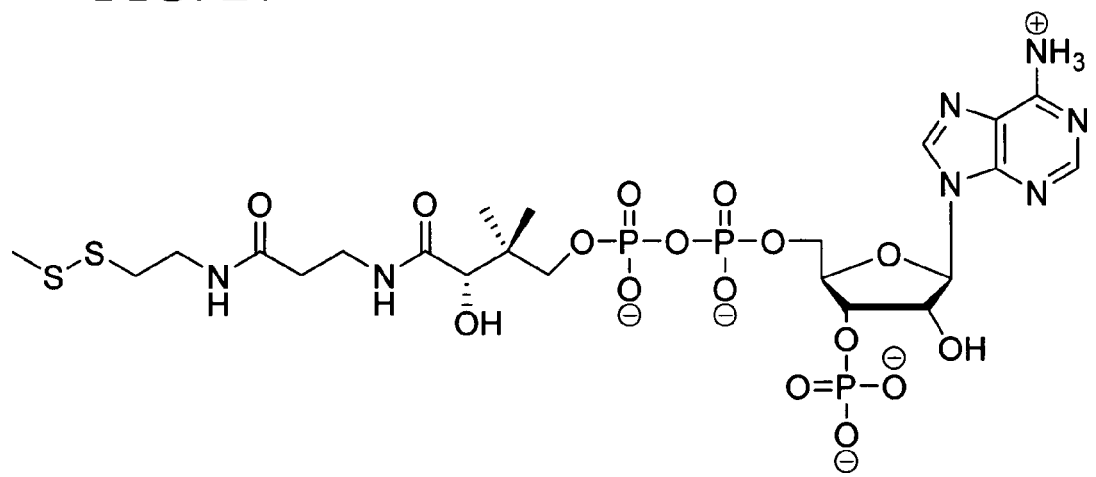
Figure 29:
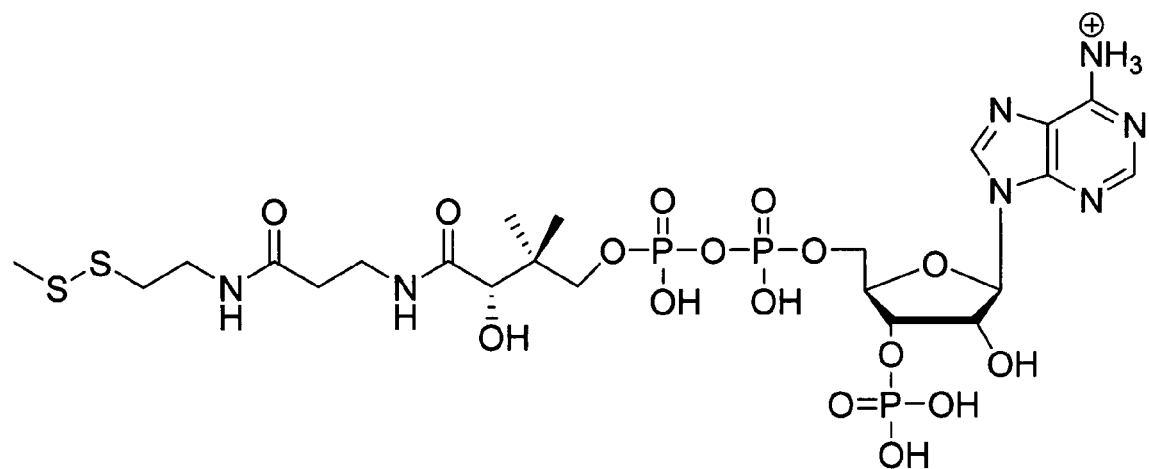
FIG. 29 shows the chemical structure of compound 28a (all sites protonated).
Figure 30:
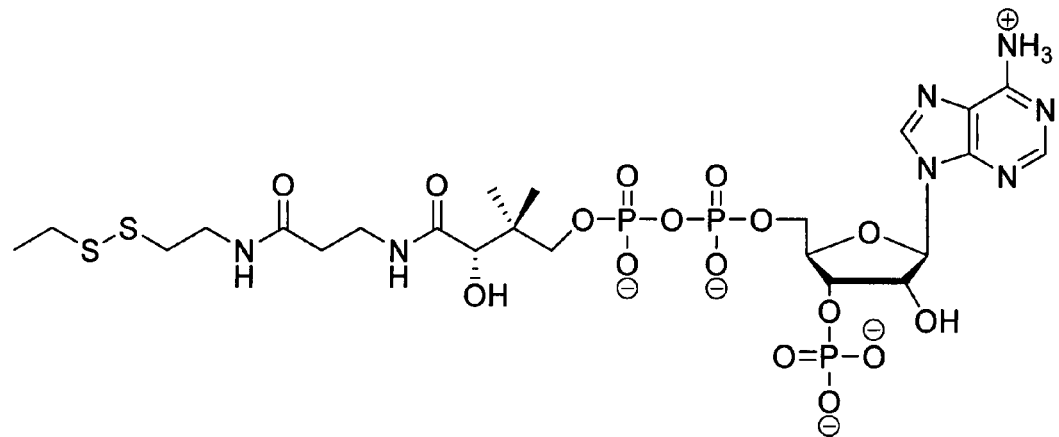
FIG. 30 shows the chemical structure of compound 28b.
Figure 31:
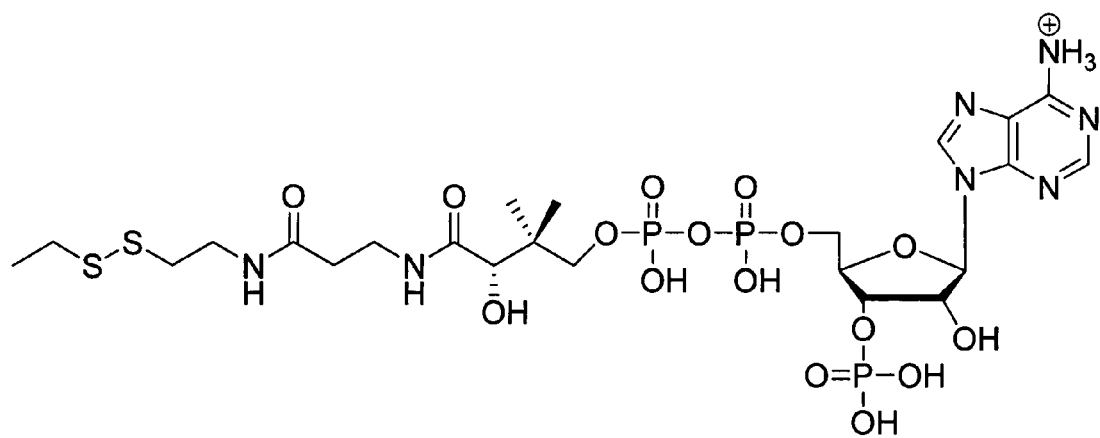
FIG. 31 shows the chemical structure of compound 28b (all sites protonated).
Figure 32:
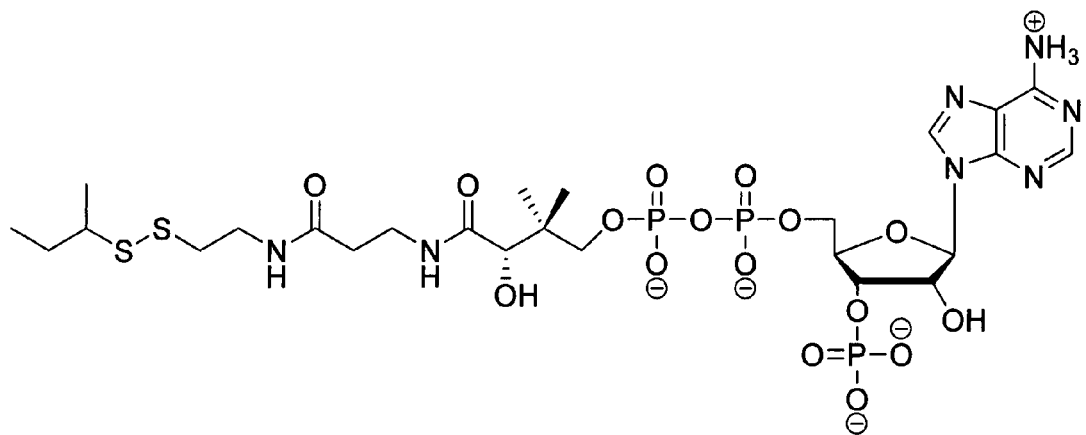
FIG. 32 shows the chemical structure of compound 28c.
Figure 33:
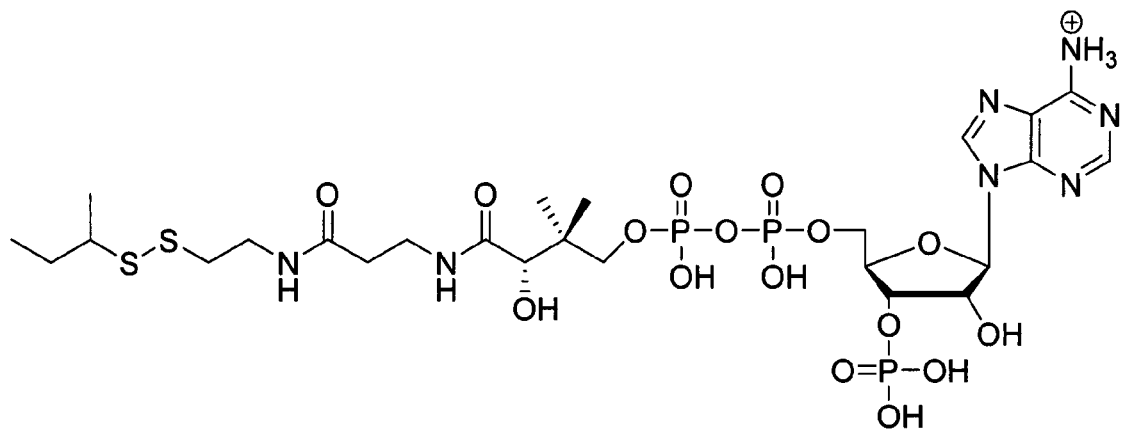
FIG. 33 shows the chemical structure of compound 28c (all sites protonated).
Figure 34:
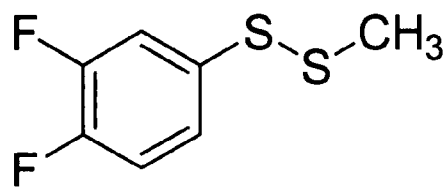
Figure 35:
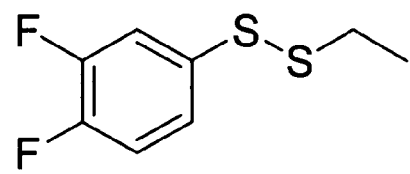
FIG. 35 shows the chemical structure of compound 33b.
Figure 36:
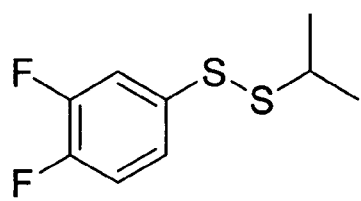
FIG. 36 shows the chemical structure of compound 33c.
Figure 37:
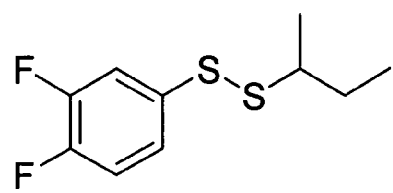
FIG. 37 shows the chemical structure of compound 33d.
Figure 38:
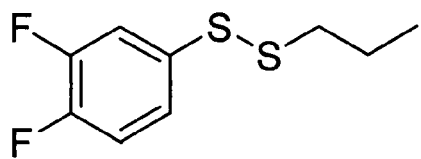
FIG. 38 shows the chemical structure of compound 33e.
Figure 39:
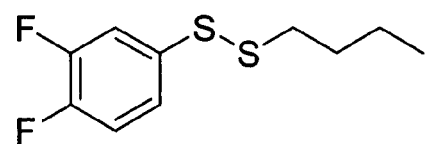
FIG. 39 shows the chemical structure of compound 33f.
Figure 40:
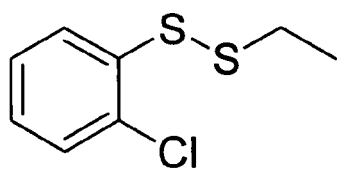
FIG. 40 shows the chemical structure of compound 34b.
Figure 41:
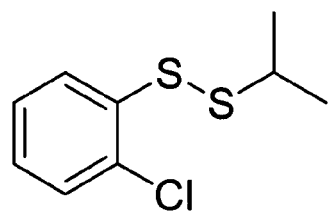
FIG. 41 shows the chemical structure of compound 34c.
Figure 42:
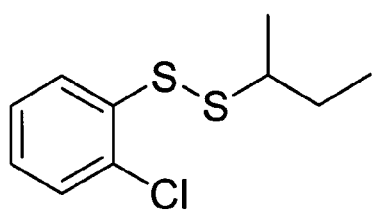
FIG. 42 shows the chemical structure of compound 34d.
Figure 43:
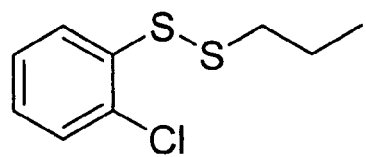
FIG. 43 shows the chemical structure of compound 34e.
Figure 44:
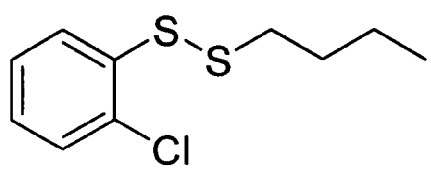
FIG. 44 shows the chemical structure of compound 34f.
Figure 45:
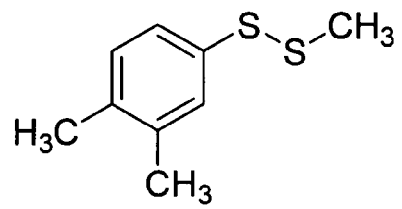
Figure 46:
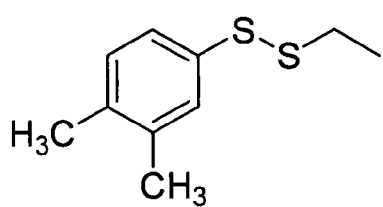
FIG. 46 shows the chemical structure of compound 35b.
Figure 47:
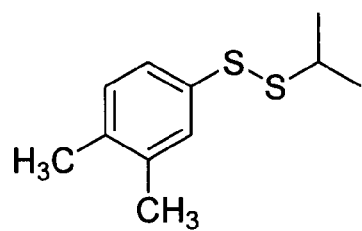
FIG. 47 shows the chemical structure of compound 35c.
Figure 48:
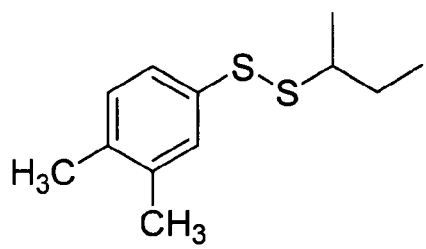
FIG. 48 shows the chemical structure of compound 35d.
Figure 49:
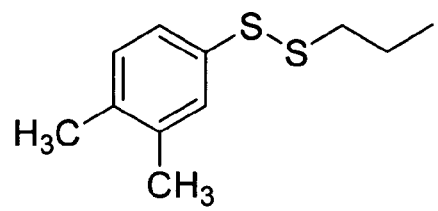
FIG. 49 shows the chemical structure of compound 35e.
Figure 50:
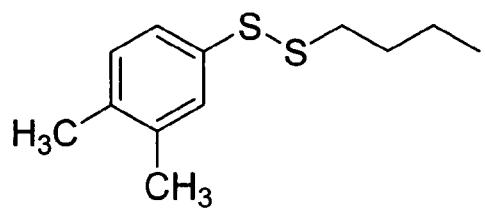
FIG. 50 shows the chemical structure of compound 35f.
Figure 51:
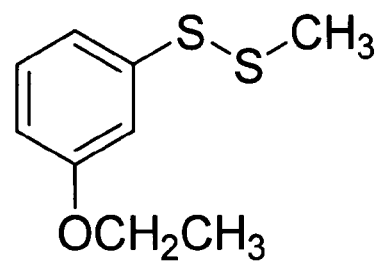
Figure 52:
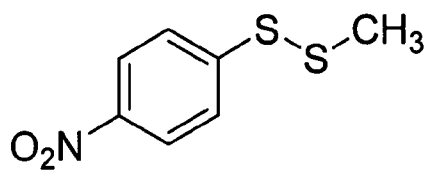
Figure 53:
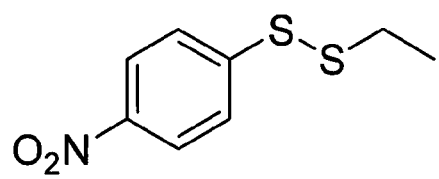
FIG. 53 shows the chemical structure of compound 38b.
Figure 54:
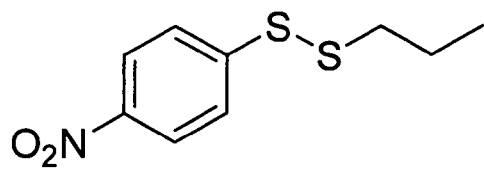
FIG. 54 shows the chemical structure of compound 38e.
Figure 55:
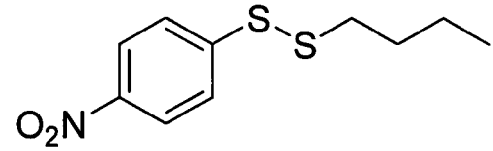
FIG. 55 shows the chemical structure of compound 38f.
Figure 56A:
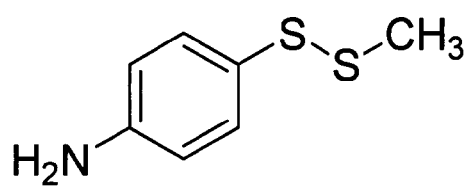
FIGS. 56A-56B show the chemical structure of compound 39a (free base, and HCl salt, respectively).
Figure 56B:
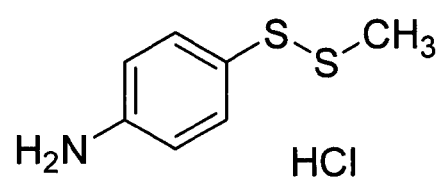
Figure 57:
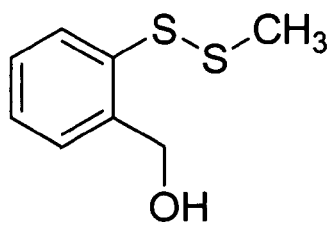
Figure 58:
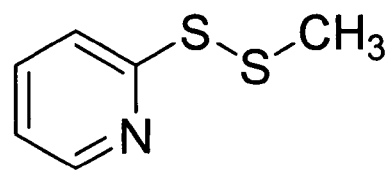
Figure 59:
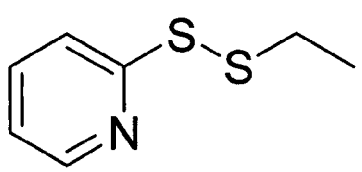
FIG. 59 shows the chemical structure of compound 42b.
Figure 60:
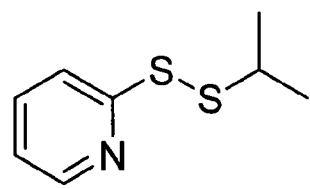
FIG. 60 shows the chemical structure of compound 42c.
Figure 61:
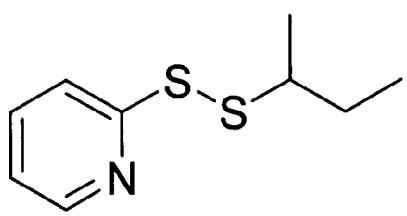
FIG. 61 shows the chemical structure of compound 42d.
Figure 62:
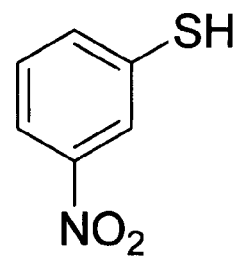
FIG. 62 shows the chemical structure of compound 43.
Figure 63:
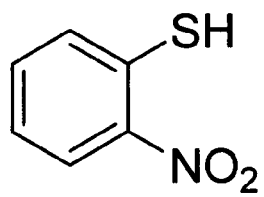
FIG. 63 shows the chemical structure of compound 44.
Figure 64:
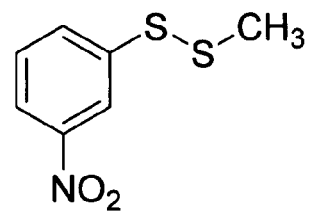
Figure 65:
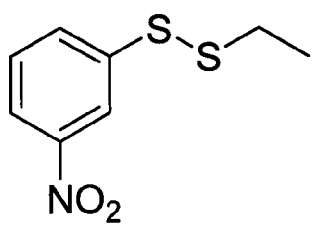
FIG. 65 shows the chemical structure of compound 43b.
Figure 66:
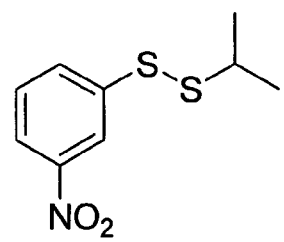
FIG. 66 shows the chemical structure of compound 43c.
Figure 67:
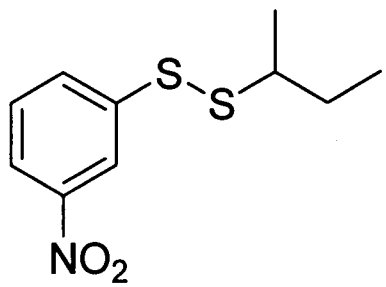
FIG. 67 shows the chemical structure of compound 43d.
Figure 68:
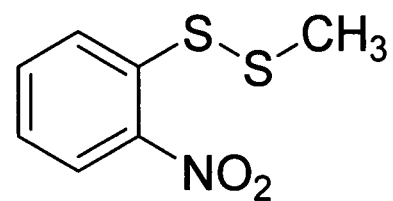
Figure 69:
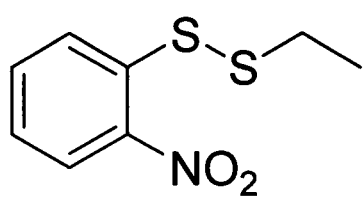
FIG. 69 shows the chemical structure of compound 44b.
Figure 70:
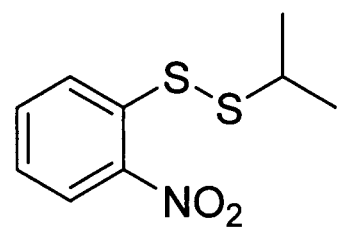
FIG. 70 shows the chemical structure of compound 44c.
Figure 71:
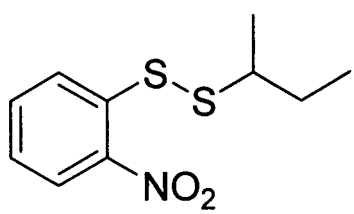
FIG. 71 shows the chemical structure of compound 44d.
Figure 72:
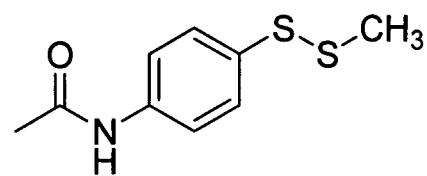
Figure 73A:
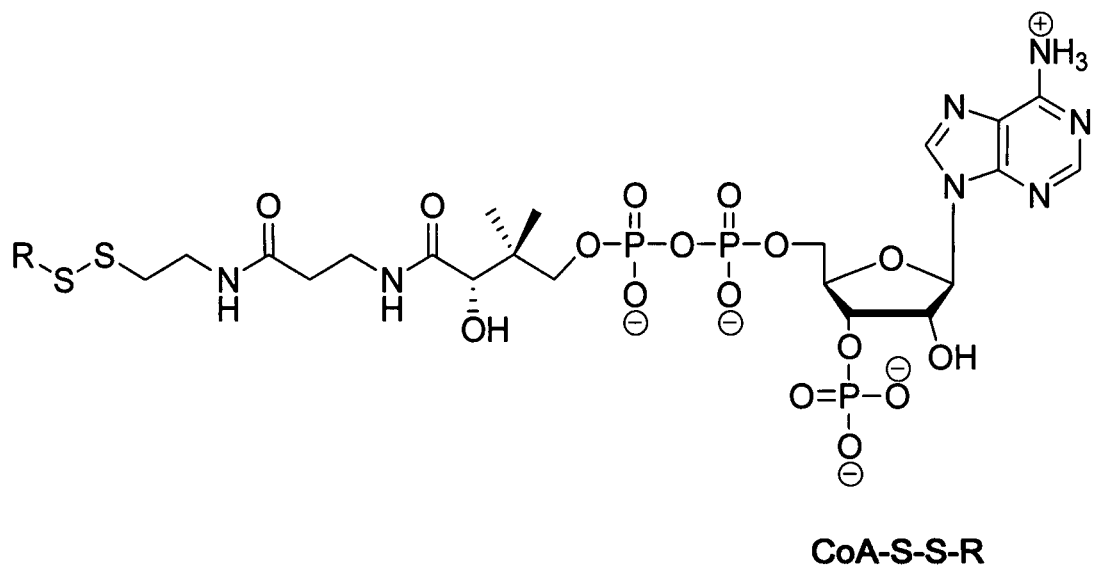
FIGS. 73A-B show the chemical structure of mixed CoA-alkyl disulfides (CoA-S—S—R.
Figure 74:
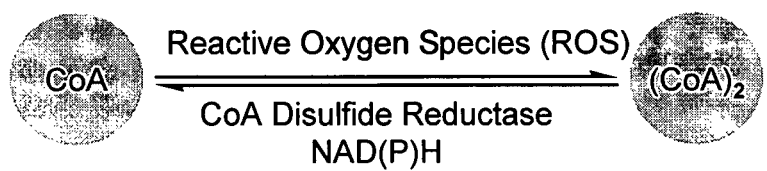
FIG. 74 demonstrates that high levels of the free thiol CoA in the two species most vulnerable to N-alkylthio β-lactams (Staphylococcus, Bacillus) correlate with CoA's role within the thiol-redox buffer. HPLC studies on S. aureus lysate have shown that N-alkylthio β-lactams do not significantly affect overall CoA levels.
Figure 73B:
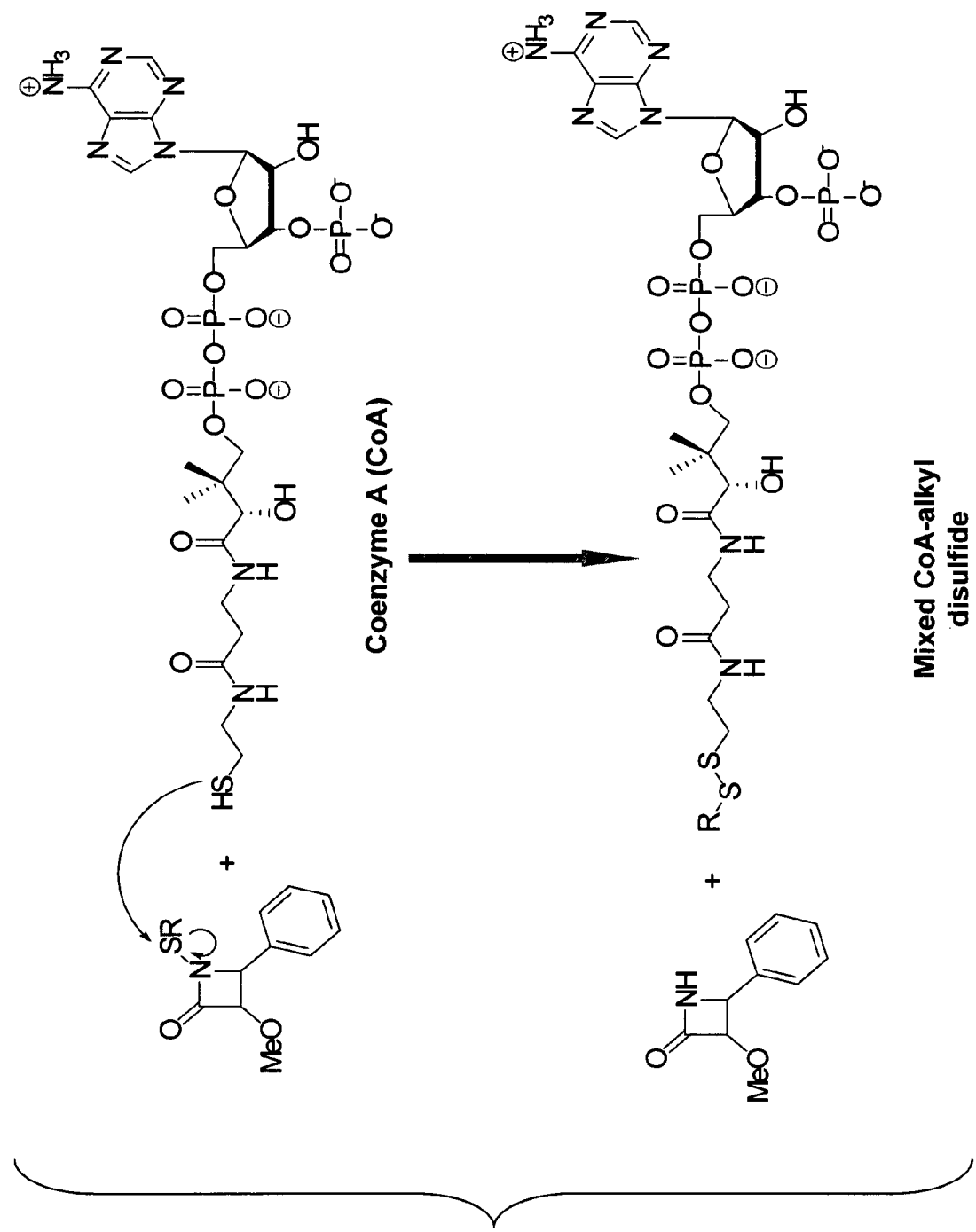
Figure 81:
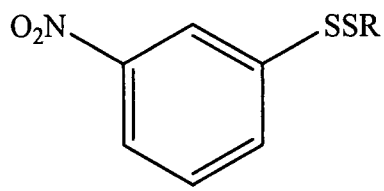
FIGS. 81-85 show disulfide compounds of the invention (compounds 22a-d, 23a-d, 24a and c, 25a and c, 26a-d, respectively, with R defined for each).
Figure 82:
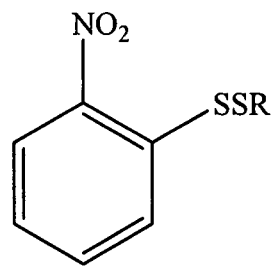
Figure 83:
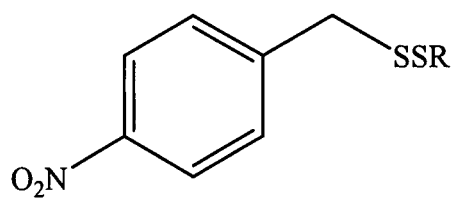
Figure 84:
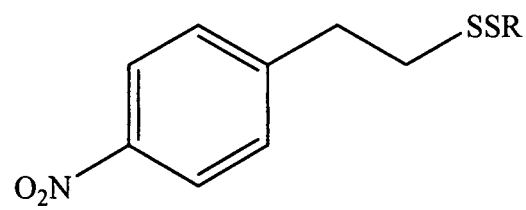
Figure 85:
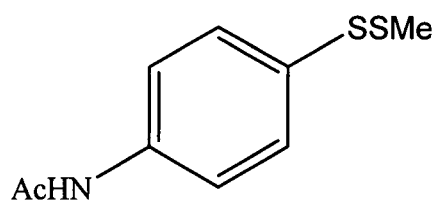
Figure 86:
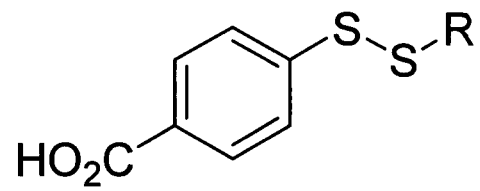
FIG. 86 shows compound 45a of the invention. R=H, alkyl, cycloalkyl, alkoxy, aryl, heteroaryl, heteroalkyl, alkanoyl, 2-aminoalkyl, 2-hydroxyalkyl, and halo; preferably, alkyl (such as methyl, ethyl, isopropyl, sec-butyl, n-propyl, n-butyl, etc.).

Relative efficacy of penicillin G, Vancomycin, N-alkylthio
β-lactam 2 g (FIG. 7B), N-alkylthio-2-oxazolidinone 13
(FIG. 17), and disulfides 38c-d (FIGS. 15A-15B, respectively)
against MSSA (ATCC 25923) and MRSA (ATCC 43300).

| Compound | PenG.[c] | Vanc. | 2 g[c] | 13 | 38c | 38d |
|---|---|---|---|---|---|---|
| Zone (MSSA)[a] | 33 | 27 | 32[c] | 29 | 47 | 67 |
| Zone (MRSA) | 14 | 22 | 34 | 28 | 70 | 54 |
| MIC (MSSA)[b] | 0.03 | 0.78[d] | 0.25 | 4 | 0.8 | 0.4 |
| MIC (MRSA) | 64 | 0.39[d] | 0.25 | 8 | — | — |

Measured against MSSA (ATCC 25923) and MRSA (ATCC 43300) unless indicated otherwise.
[a]Zone of inhibition (mm) as measured by Kirby-Bauer disk diffusion assay.
[b]Minimum inhibitory concentration (μg/mL).
[c]Data taken from ref. 6.
[d]Data for vancomycin against MSSA (ATCC 25923) and MRSA 67, as reported by ref. 52.

Analysis of the Kirby-Bauer and MIC data for the nitrophenyl disulfides shows that for both the para and meta substituted series, the isopropyl and sec-butyl disulfides perform the best against both MRSA and MSSA. With the ortho series, the methyl disulfide exhibits the greatest activity.

Figure 16A:
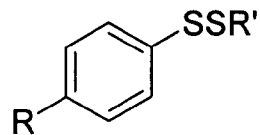
FIGS. 16A-B show sulfonates, phosphates, and carboxylates, representing alkyl p-nitrophenyl disulfide analogs 47-50, and 51-54, respectively.
Figure 16B:
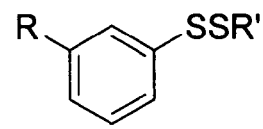

It is not clear what causes this remarkable potency in the nitrophenyl disulfides. However, several postulates can be made: (1) The nitro group serves to enhance water solubility of the disulfides, allowing the molecules to move more freely into the cytosol. (2) The more lipophilic molecules (lacking the nitro moiety) are not able to stay in aqueous solution, or may remain sequestered in the cell membrane, thus reducing their availability to FabH. (3) The electron-withdrawing nitro groups make the disulfides more susceptible to attach by the cysteine thiolate. (4) The nitro substituent may be essential for the molecule to bind to the enzyme active site. In order to evaluate these possibilities, co-crystallization studies and in vitro studies with FabH are underway in the Reynolds laboratory. Additionally, several geometrically and electronically similar compounds, such as the sulfonates, phosphates, and carboxylates (47-54, FIGS. 16A-B) are being explored.

EXAMPLE 4

Activity Against *Bacillus*

The activity of these disulfide compounds against *Bacillus anthracis* was also evaluated. Results of Kirby-Bauer and MIC studies are shown in Table 10 and Table 11, respectively.

TABLE 10

Zones of growth inhibition (mm) of *B. anthracis*
(USF 848) for aryl-alkyl disulfides.

|   | 38 | 42 | 43 | 44 | 46 |
|---|---|---|---|---|---|
| a | 47(54)[a] | — | 43 | 31 | (23) |
| b | 56(67) | (27) | 32(40) | 35 | — |
| c | 71 | (16) | 30(54) | 16(27) | — |
| d | 56(62) | (17) | 27(41) | 23 | — |
| e | 49(57) | — | — | — | — |
| f | 44(52) | — | — | — | — |

In each case, 20 μg of the test compound in DMSO was added to wells prior to incubation. The values presented correspond to the average zone diameter in mm (duplicate experiments) for the zone of growth inhibitions observed after 24 h of incubation at 37° C. Errors values are within ±1 mm. [a.]Numbers in parentheses represent areas of partial growth inhibition.

TABLE 11

Minimum inhibitory concentration (MIC) values (μg/mL)
of active compounds against *B. anthracis* (USF 848).

|   | 38 | 43 | 44 | 46 |
|---|---|---|---|---|
| a | 0.25 | 2 | 4 | 8 |
| b | 0.25 | 0.38 | 0.63 | — |
| c | <0.125 | <0.125 | 0.63 | — |
| d | <0.125 | <0.125 | 0.75 | — |
| e | 1 | — | — | — |
| f | 1 | — | — | — |

The values presented are the lowest concentration of drug (in μg/mL) where bacterial growth is visibly inhibited. Values were determined by serial dilution in a 24-well plate according to NCCLS protocols (National Committee for Clinical Laboratory Standards, Methods for Dilution of Antimicrobial Susceptibility Tests for Bacteria that Grow Aerobically; NCCLS Document M7-A4, 1997, Vol. 17(2)).

The activity of these compounds against *B. anthracis* mimics that observed against *S. aureus*: the para and meta compounds outperform the ortho isomers, and the isopropyl and sec-butyl disulfides exhibit the greatest activity. The potency observed for these compounds is remarkable. The MIC values observed for 38c, 38d, 43c, and 43d are comparable to the reported value for Ciprofloxacin (0.094 for 50% growth inhibition) (Coker, P. R. et al. *Antimicro. Agents Chemother.*, 2002, 46(12):3843-3845).

EXAMPLE 5

Activity Against *E. coli*

None of the N-alkylthio β-lactams or N-alkylthio-2-oxazolidinones produced in the Turos group have ever shown any activity against *E. coli*. This has been postulated to be a result of the high glutathione levels relative to CoA in this species, so that the easily-reduced glutathione disulfides are formed in favor of CoA disulfides. However, since 33-46 were designed to act directly on FabH without interacting with CoA or glutathione, it was proposed that these compounds might exhibit activity against *E. coli*.

Indeed, these compounds, particularly the p-nitrobenzene series (38a-f), do exhibit activity against *E. coli* (K12 strain, ATCC23590). This data is summarized in Table 12.

The meta and ortho-nitrobenzene disulfides were also tested against *E. coli*, but showed less activity than the para isomers: compounds 43a and 44a showed a zone of inhibition of 10 mm and 9 mm, respectively. Compounds with alkyl groups larger than methyl showed no activity.

TABLE 12

Kirby-Bauer zones of inhibition (mm) and minimum inhibitory
concentration values (μg/mL) (MICs) for compounds
38a-f against *E. coli* (K12; ATCC 23590).

|   | Zone of Inhibition (mm) | MIC (μg/mL) |
|---|---|---|
| 38a | 17 (24) | 16 |
| 38b | 15 (23) | 16 |
| 38c | (11) | 96 |
| 38d | (10) | 128 |
| 38e | 16 (21) | 64 |
| 38f | 15 (22) | 96 |

Kirby-Bauer tests were run as described above, except using *E. coli*, K12 strain. Numbers in parentheses represent zones of partial inhibition.

It is interesting to note that the trends in activity observed for the nitrophenyl disulfides exactly parallel previous observations on the relative size of the active site in each of the strains studied. The active site of the *E. coli* FabH has been reported to react preferentially to acetyl CoA over larger or branched acyl CoA analogs (Heath, R. J. and Rock, C. O. *J. Biol. Chem.*, 1996, 271(18):10996-11000). By contrast, the FabH from both *Staphylococcus* (He, X. and Reynolds, K. A. *Antimicrob. Agents Chemother.*, 2002, 46(5):1310-1318) and *Bacillus* (Choi, K-H. et al. *J. Bacteriology*, 2000, 182(2):365-370) have been reported to have larger active-site pockets, which favor reactions with branched acyl-CoA species such as isobutyryl-CoA (He, X. and Reynolds, K. A. *Antimicrob. Agents Chemother.*, 2002, 46(5):1310-1318).

These trends are followed precisely in the bioactivities of the disulfide series, providing strong indirect evidence that these compounds do, in fact, inhibit FabH. This data is summarized in Table 13.

TABLE 13

Minimum inhibitory concentration (MIC) values (µg/mL) of the p-nitrophenyl disulfide series (38a-f) against *S. aureus, B. anthracis,* and *E. coli*.

| Compound | *S. aureus* (ATCC 25923) | *B. anthracis* (USF 848) | *E. coli* (ATCC 23590) |
|---|---|---|---|
| 38a | 16 | 0.25 | 16 |
| 38b | 32 | 0.25 | 16 |
| 38c | 0.4 | <0.125 | 96 |
| 38d | 0.8 | <0.125 | 128 |
| 38e | 24 | 1 | 64 |
| 38f | 32 | 1 | 96 |

MIC indicates the lowest concentration of drug (in µg/mL) where bacterial growth is visibly inhibited.

The fact that the aryl-alkyl disulfides are less active against *E. coli* than against *S. aureus* or *B. anthracis* may be due to differences in the thiol-redox buffers (Argyrou, A. and Blanchard, J. S. *Prog. Nucl. Acid Res. Mol. Biol.,* 2004, 78:89-142; Poole, L. B. et al. *Ann. Rev. Pharmacol. Toxic.,* 2004, 44:325-347). *Staphylococcus* and *Bacillus* utilize a coenzyme-A based thiol-redox buffer, while *E. coli* uses a glutathione buffer. Coenzyme A disulfide reductase (CoADR) has been reported to be much more selective than glutathione disulfide reductase (GDR) (delcardayre, S. B. et al. *J. Biol. Chem.,* 1998, 273(10):5744-5751). Thus, the active disulfides may be more easily reduced in *E. coli*. If so, this suggests that the aryl-alkyl disulfides will be less cytotoxic to eukaryotic cells, which also utilize a glutathione buffer.

EXAMPLE 6

Inhibition of Purified FabH

Inhibition experiments on *E. coli* FabH verify that disulfides 38a-f are extremely active against this enzyme. Each compound in this series showed >90% inhibition of *E. coli* FabH at a disulfide concentration of 5 µM (Table 14).

TABLE 14

Percent inhibition[a] of FabH derived from *E. coli* by disulfides 38a-f.

| Compound | ecFabH (%) |
|---|---|
| 38a | 94 |
| 38b | 98 |
| 38c | 98.5 |
| 38d | 96 |
| 38e | 91 |
| 38f | 93 |

Measured as the percent decrease in activity of FabH in the presence of 5 µM of test compounds, as compared to the same enzyme in the absence of test compounds.

The design of FabH inhibitors using the model of the CoA disulfides has been stunningly successful. From a relatively small set of very simple disulfides, several compounds with nanomolar activities against *S. aureus* and *B. anthracis* have been produced. These compounds exhibit potency which is comparable to that of several drugs currently on the market.

The p- and m-nitrophenyl alkyl disulfides are the most potent disulfides synthesized thus far. Preliminary biological results suggest that these compounds may be "tuned" for optimal efficacy against a particular strain: For *E. coli*, the methyl disulfides are optimal. For *Staphylococcus* and *Bacillus*, the isopropyl- and s-butyl disulfides appear to be best. Based on the results described above, it is suspected that longer-chain disulfides may be optimal against *M. tuberculosis*.

In light of the pressing need for new antibacterial compounds, particularly those effective against MRSA and *B. anthracis* (Garrett, L. *The Coming Plague*, Penguin Books: New York, 1994; Lowry, F. *New Eng J. Med.,* 1998, 339:520-532), these simple disulfide compounds may represent a critical advance in the battle against infectious disease. It is therefore very important to continue the development of these compounds, and to more fully evaluate their potential as a new generation of commercial anti-infectives.

The compounds of the present invention (also referred to herein as N-alkylthio β-lactams, alkyl-coenzyme A asymmetric disulfides, and aryl-alkyl disulfides) exhibit antibacterial activity against bacteria such as MRSA and anthrax. Because of their powerful antibacterial properties, the present compounds may also be used to supplement feed for animals.

In addition, the compounds of the present invention that exhibit antibacterial activity may also be used as medicaments, and also as substances for preserving inorganic and organic materials, especially organic materials of all kinds, for example, polymers, lubricants, paints, fibers, leather, paper, timber, foodstuffs, and water. For example, these compounds can be covalently bonded to the polymer.

The compounds of the present invention may also be used to prevent, alleviate, or cure diseases caused by pathogens whose growth is inhibited by these compounds. The instant compounds are particularly active against bacteria and bacteria-like microorganisms. They are therefore suitable for use in human and veterinary medicine, for the prophylaxis and chemotherapy of local and systemic infections caused by these pathogens. As used herein, the terms "treat", "treating", and "treatment" include therapy that alleviates one or more symptoms caused by the infection, or that cures the underlying infection. As used herein, the terms "prevent", "preventing", and "prevention" include prophylaxis, complete prevention, or delaying onset of the infection or delaying onset of one or more symptoms caused by the infection. Optionally, the method further comprises identifying the human or non-human subject as one suffering from a specific or non-specific bacterial infection. The presence of bacterial infection can be determined using methods known to those of ordinary skill in the art of clinical diagnosis of disease (e.g., infectious disease).

The invention further encompasses methods for inhibiting the growth of bacteria by contacting the bacteria with an effective amount of the compounds of the invention in vitro or in vivo, or by applying the compound to a substrate (surface) likely to come in contact with the bacteria, such as a work surface, table, surgical instrument, implant or other device to be placed in or on the body (i.e., foreign object to be inserted into a subject, such as a stent, catheter, access port, intravenous delivery tube (Hickman), heart valve, dental implant, electro-mechanical device, prosthetic device, glucose sensor, or stabilizing device such as orthopedic nails and pins), eating or cooking utensil, etc.

The compounds of the present invention include all hydrates and salts of the N-alkylthio β-lactams and disulfide compounds (e.g., alkyl-coenzyme A asymmetric disulfides or aryl-alkyl disulfides) that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the present invention can be formulated as pharmaceutical compositions and administered to a patient, such as a human patient, in a variety of forms adapted to the chosen route of administration, e.g., orally or parenterally, by intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or other suitable solvent, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient presenting the previously sterile-filtered solutions.

For topical administration, the present compounds may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from adsorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art (U.S. Pat. No. 4,938,949 (Borch et al.)).

Accordingly, the invention includes a pharmaceutical composition comprising a compound of the present invention as described above; or a pharmaceutically acceptable salt thereof, in combination with a pharmaceutically acceptable carrier. Pharmaceutical compositions adapted for oral, topical or parenteral administration, comprising an amount of one or more compounds effective to treat a bacterial infection, are a preferred embodiment of the invention.

The following definitions are used, unless otherwise described. Halo is fluoro, chloro, bromo, or iodo. "Alkyl," "alkoxy," etc. denote both straight and branched groups; but reference to an individual radical such as "propyl" embraces only the straight chain radical, a branched chain isomer such as "isopropyl" being specifically referred to. "Aryl" denotes a phenyl radical or an ortho-fused bicyclic carbocyclic radical having about nine to ten ring atoms in which at least one ring is aromatic. "Heteroaryl" encompasses a radical attached via a ring carbon of a monocyclic aromatic ring containing five or six ring atoms consisting of carbon and one to four heteroatoms each selected from the group consisting of non-peroxide oxygen, sulfur, and $N(R_x)$ wherein $R_x$ is absent or is hydrogen, oxo, alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. "Heteroalkyl" encompasses the replacement of a carbon atom within an alkyl chain with a heteroatom; e.g., replacement with an element other than carbon such as N, S, or O, including both an alkyl interrupted by a heteroatom as well as an alkyl substituted by a heteroatom.

It will be appreciated by those skilled in the art that compounds of the invention having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase), and how to determine antibacterial activity using the tests described herein, or using other tests which are well known in the art.

Specific and preferred values listed below for radicals, substituents, and ranges, are for illustration only; they do not exclude other defined values or other values within defined ranges for the radicals and substituents.

Specifically, "alkyl" can include, for example, methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl or pentadecyl; "alkenyl" can include vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradecenyl, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, 14-pentadecenyl; "alkoxy" can include methoxy, ethoxy, propoxy, isopropoxy, butoxy, isobutoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy; "alkanoyl" can include acetyl, propanoyl, butanoyl, pentanoyl, hexanoyl, heptanoyl, octanoyl, nonanoyl, decanoyl, undecanoyl, dodecanoyl, tridecanoyl, tetradecanoyl, or pentadecanoyl; "cycloalkyl" can include cyclopropyl, cyclobutyl, cyclopentyl, cyclohexyl, cycloheptyl, or cyclooctyl. "Aryl" can include phenyl, indenyl, 5,6,7,8-tetrahydronaphthyl, or naphthyl. "Heteroaryl" can include furyl, imidazolyl, tetrazolyl, pyridyl, (or its N-oxide), thienyl, pyrimidinyl (or its N-oxide), indolyl, or quinolyl (or its N-oxide).

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state. Preferably, the compound of the invention (N-alkylthio β-lactam or disulfide compound) is administered in an isolated or pure form.

As used in this specification, the singular forms "a", "an", and "the" include plural reference unless the context clearly dictates otherwise. Thus, for example, a reference to "a microorganism" includes more than one such microorganism. A reference to "a cell" includes more than one such cell, and so forth. A reference to "a compound" includes more than one such compound.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification Principles and Practice (2nd ed., Springer-Verlag); and PCR: A Practical Approach (McPherson et al. Eds. (1991) IRL Press)), each of which are incorporated herein by reference in their entirety.

U.S. Pat. No. 6,476,015 (Turos et al.), filed Jul. 24, 2000, and U.S. Pat. No. 6,946,458 (Turos), filed Nov. 5, 2002, and U.S. Pat. No. 7,026,472 (Dou et al.), filed May 6, 2003, which describe N-thiolated β-lactam compounds useful in the carrying out the methods of the invention, are each incorporated herein by reference in their entirety. Mishra, R. K. et al. *Bioorg Med. Chem. Lett.,* 2006, 16:2081-208; Turos, E. et al. *Bioorg. Med. Chem. Lett.,* 2007, 17:53-56; Mishra, R. K. et al. *Organic Lett.,* 2007, 9(4):575-578; and Revell, K. D. et al. *Bioorg. Med. Chem.,* 2007, 15:2453-2467, which describe N-thiolated beta-lactams, N-thiolated oxazolidinones, and antibiotic-conjugated nanoparticles, and uses thereof, are incorporated herein by reference in their entirety.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A compound having a chemical structure of:

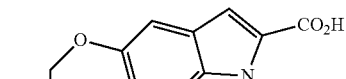
32

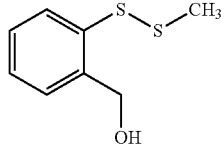
41a

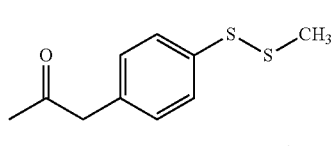
46a

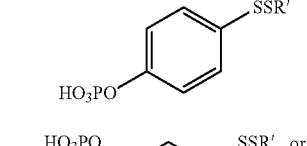
48

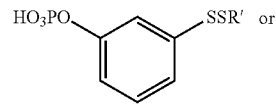
52

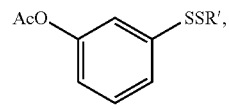
53 or a pharmaceutically acceptable salt thereof, wherein R and R' are the same or different, each being independently selected from the group consisting of H, alkyl, cycloalkyl, alkoxy, aryl, heteroaryl, heteroalkyl, alkanoyl, 2-aminoalkyl, 2-hydroxyalkyl, and halo.

2. A composition comprising a compound having a chemical structure of:

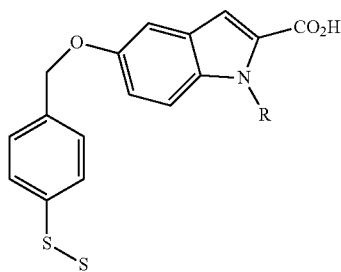
32

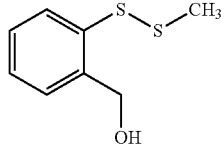
41a

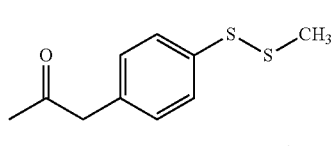
46a

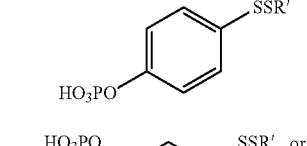
48

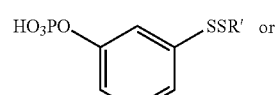
52

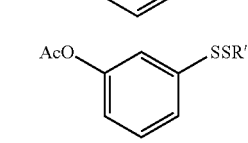
53 or a pharmaceutically acceptable salt thereof, wherein R and R' are the same or different, each being independently selected from the group consisting of H, alkyl, cycloalkyl, alkoxy, aryl, heteroaryl, heteroalkyl, alkanoyl, 2-aminoalkyl, 2-hydroxyalkyl, and halo; and a pharmaceutically acceptable carrier.

3. The composition of claim 2, further comprising an additional antibiotic agent.

4. The composition of claim 2, wherein said composition is formulated for feeding to livestock.

5. A kit comprising a compound having a chemical structure of:

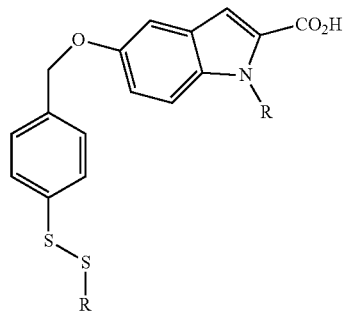

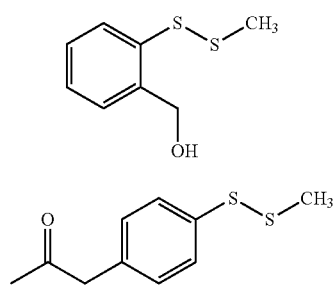

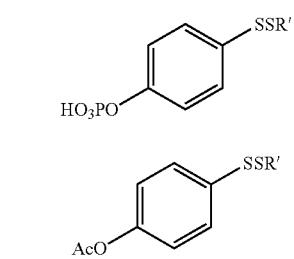

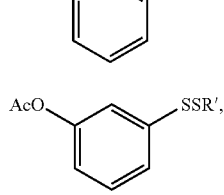

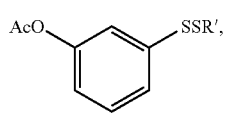

or a pharmaceutically acceptable salt thereof, wherein R and R' are the same or different, each being independently selected from the group consisting of H, alkyl, cycloalkyl, alkoxy, aryl, heteroaryl, heteroalkyl, alkanoyl, 2-aminoalkyl, 2-hydroxyalkyl, and halo.

6. The kit of claim 5, wherein said kit further comprises an antibiotic agent.

7. The kit of claim 5, wherein said kit further comprises a pharmaceutically acceptable carrier.

8. A compound having a chemical structure of:

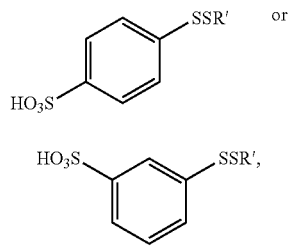

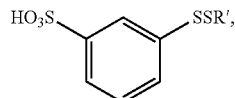

or a pharmaceutically acceptable salt thereof, wherein R' is selected from the group consisting of H, alkyl, cycloalkyl, alkoxy, aryl, heteroaryl, alkanoyl, and halo.

9. A composition comprising a compound having a chemical structure of:

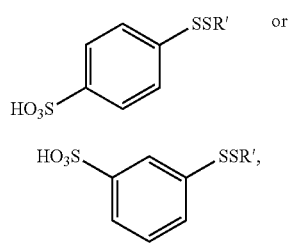

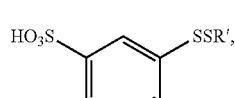

or a pharmaceutically acceptable salt thereof, wherein R' is selected from the group consisting of H, alkyl, cycloalkyl, alkoxy, aryl, heteroaryl, alkanoyl, and halo; and a pharmaceutically acceptable carrier.

10. The composition of claim 9, further comprising an additional antibiotic agent.

11. The composition of claim 9, wherein said composition is formulated for feeding to livestock.

12. A kit comprising a compound having a chemical structure of:

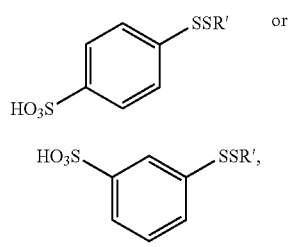

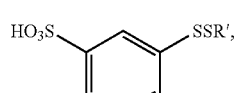

or a pharmaceutically acceptable salt thereof, wherein R' is selected from the group consisting of H, alkyl, cycloalkyl, alkoxy, aryl, heteroaryl, alkanoyl, and halo.

13. The kit of claim 12, wherein said kit further comprises an antibiotic agent.

14. The kit of claim 12, wherein said kit further comprises a pharmaceutically acceptable carrier.

15. A compound having a chemical structure of:

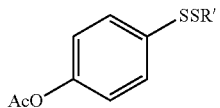
49 or a pharmaceutically acceptable salt thereof, wherein R' is selected from the group consisting of H, cycloalkyl, alkoxy, heteroaryl, heteroalkyl, alkanoyl, 2-aminoalkyl, 2-hydroxyalkyl, and halo.

16. A composition comprising a compound having a chemical structure of:

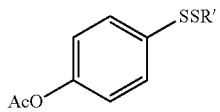
49 or a pharmaceutically acceptable salt thereof, wherein R' is selected from the group consisting of H, cycloalkyl, alkoxy, heteroaryl, heteroalkyl, alkanoyl, 2-aminoalkyl, 2-hydroxyalkyl, and halo; and a pharmaceutically acceptable carrier.

17. A kit comprising a compound having a chemical structure of:

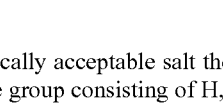
49 or a pharmaceutically acceptable salt thereof, wherein R' is selected from the group consisting of H, cycloalkyl, alkoxy, heteroaryl, heteroalkyl, alkanoyl, 2-aminoalkyl, 2-hydroxyalkyl, and halo.

18. A method for treating a bacterial infection, comprising administering to a subject in need thereof an effective amount of a compound having a chemical structure of:

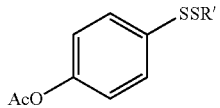
32

-continued

41a

46a

48

49

52

53 or a pharmaceutically acceptable salt thereof, wherein R and R' are the same or different, each being independently selected from the group consisting of H, alkyl, cycloalkyl, alkoxy, aryl, heteroaryl, heteroalkyl, alkanoyl, 2-aminoalkyl, 2-hydroxyalkyl, and halo; or a compound having a chemical structure of:

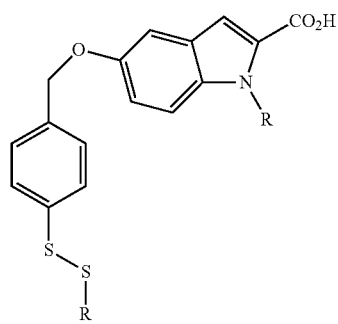

47

51 or a pharmaceutically acceptable salt thereof, wherein R' is selected from the group consisting of H, alkyl, cycloalkyl, alkoxy, aryl, heteroaryl, heteroalkyl, alkanoyl, and halo; or a composition comprising said compound.

19. The method of claim 18, wherein the bacteria is *Staphylococcus, Bacillus, Micrococcus, Streptococcus, Neisseria, Streptomyces*, or *Mycobacterium tuberculosis*.

20. The method of claim 18, wherein the bacteria is methicillin-susceptible *Staphylococcus aureus* (MSSA) or methicillin-resistant *Staphylococcus aureus* (MRSA).

21. The method of claim 18, wherein the bacteria is *Bacillus anthracis*.

22. The method of claim 18, wherein the bacteria is *Escherichia coli*.

23. The method of claim 18, wherein said administering is carried out by a route selected from the group consisting of oral, intravenous, and topical.

24. A method for inhibiting the growth of bacteria, comprising contacting the bacteria with an effective amount of a compound having a chemical structure of:

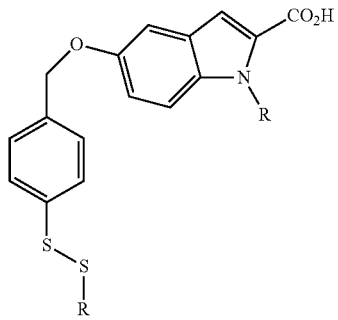

32

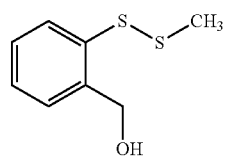

41a

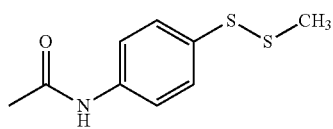

46a

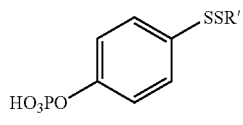

48

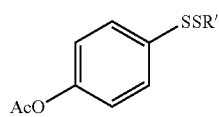

49

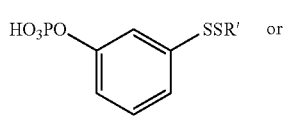

52

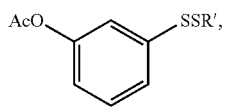

53 or a pharmaceutically acceptable salt thereof, wherein R and R' are the same or different, each being independently selected from the group consisting of H, alkyl, cycloalkyl, alkoxy, aryl, heteroaryl, heteroalkyl, alkanoyl, 2-aminoalkyl, 2-hydroxyalkyl, and halo; or a compound having a chemical structure of:

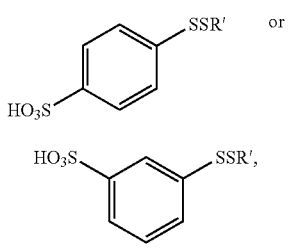

47

51 or a pharmaceutically acceptable salt thereof, wherein R' is selected from the group consisting of H, alkyl, cycloalkyl, alkoxy, aryl, heteroaryl, heteroalkyl, alkanoyl, and halo; or a composition comprising said compound.

25. The method of claim 24, wherein the bacteria is *Staphylococcus, Bacillus, Micrococcus, Streptococcus, Neisseria, Streptomyces*, or *Mycobacterium tuberculosis*.

26. The method of claim 24, wherein the bacteria is methicillin-susceptible *Staphylococcus aureus* (MSSA) or methicillin-resistant *Staphylococcus aureus* (MRSA).

27. The method of claim 24, wherein the bacteria is *Bacillus anthracis*.

28. The method of claim 24, wherein the bacteria is *Escherichia coli*.

* * * * *

UNITED STATES PATENT AND TRADEMARK OFFICE
CERTIFICATE OF CORRECTION

PATENT NO. : 8,722,937 B2
APPLICATION NO. : 11/712305
DATED : May 13, 2014
INVENTOR(S) : Edward Turos and Kevin D. Revell It is certified that error appears in the above-identified patent and that said Letters Patent is hereby corrected as shown below:

In the Specification:

Column 19,
Line 9, "1-μL" should read --1-30 μL--

Column 20,
Line 3, "[1-$^{17}$C]" should read --[1-$^{14}$C]--

Column 22,
Line 55, "strains. This" should read --strains $^c$ This--

Column 25,
Line 45, "(delcardayre," should read --(delCardayre,--

Column 31,
Line 60,

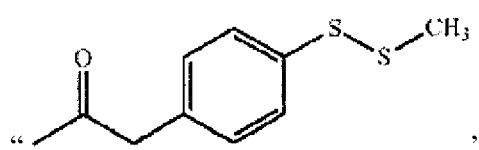 " should read -- 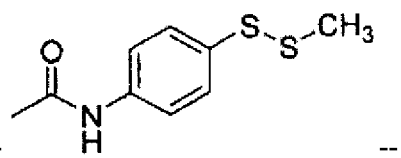 --

In the Claims:

Column 32,
Line 45,

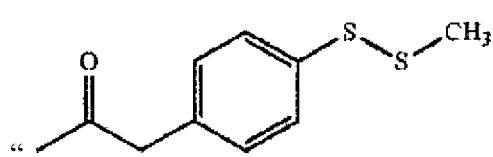 " should read -- 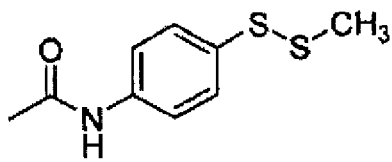 --

Signed and Sealed this
Twelfth Day of May, 2015

Michelle K. Lee
*Director of the United States Patent and Trademark Office*

CERTIFICATE OF CORRECTION (continued)
U.S. Pat. No. 8,722,937 B2

Column 33,
Line 30,

" 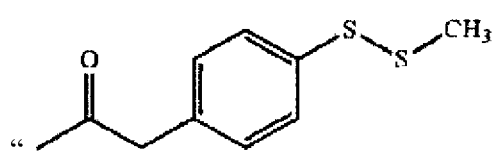 " should read -- 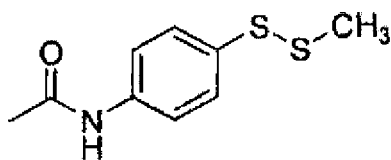 --

Column 33,
Line 40,

" 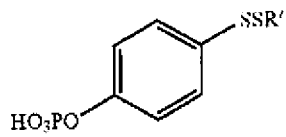

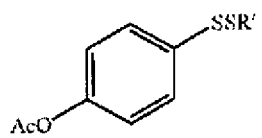

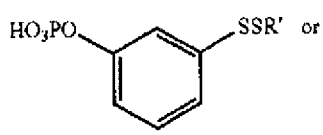 " should read -- 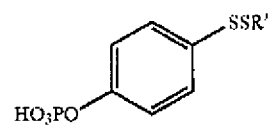

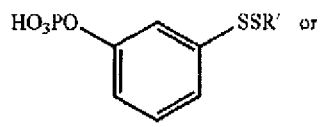 --

Column 33,
Line 49,

" 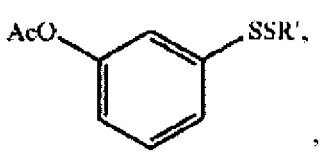 " should read -- 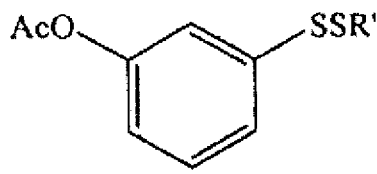 --